(12) United States Patent
Kim et al.

(10) Patent No.: US 6,790,937 B2
(45) Date of Patent: Sep. 14, 2004

(54) RECOMBINANT SCFV ANTIBODIES SPECIFIC TO EIMERIA SPP. RESPONSIBLE FOR COCCIDIOSIS

(75) Inventors: Jin-Kyoo Kim, Kyongsangnam-do (KR); Jae-Yong Han, Seoul (KR); Ki-Duck Song, Daejon Metropolitan (KR); Sung-Won Kim, Kyongsangnam-do (KR); Won-Gi Min, Beltsville, MD (US); Eun-Jung Son, Beltsville, MD (US); Hyun Soon Lillehoj, Beltsville, MD (US); Erik Peter Lillehoj, Beltsville, MD (US)

(73) Assignee: Avicore Biotechnology Institute Inc. (KR)

( * ) Notice: Subject to any disclaimer, the term of this patent is extended or adjusted under 35 U.S.C. 154(b) by 73 days.

(21) Appl. No.: 10/083,424

(22) Filed: Feb. 26, 2002

(65) Prior Publication Data

US 2003/0104497 A1 Jun. 5, 2003

(30) Foreign Application Priority Data

Aug. 30, 2001 (KR) .......................................... 2001-52934

(51) Int. Cl.[7] .......................... C12P 21/08; C12P 21/06; C12P 21/02; C07K 16/00; A61K 39/012
(52) U.S. Cl. ................................. 530/387.3; 530/388.6; 530/822; 530/350; 530/387.1; 435/69.1; 435/69.7; 435/342; 435/320.1; 435/258.4; 536/23.5; 536/23.7; 536/23.53; 536/24.32; 424/267.1; 424/184.1; 424/271.1; 514/44; 514/24; 514/23
(58) Field of Search ............................ 530/387.3, 388.6, 530/822, 387.1, 350; 435/342, 320.1, 258.4, 69.1, 69.7; 536/23.5, 23.7, 24.32, 23.53; 424/267.1, 271.1, 184.1; 516/46, 26, 23

(56) References Cited

PUBLICATIONS

Lillehoj et al Clinical Microbiology reviews 1996, 9; 349–360.*

Rudikoff et al, Proc Natl Acad Sci USA 1982, vol. 79 p. 1979.*

Ki Duk Song, et al., Molecular Cloning and Characterization of cDNA Encoding Immunoglobulin Heavy and Light chain Variable Regions from Four Chicken Monoclonal Antibodies Specific to Surface Antigens of Intestinal Parasite, Eimeria acervulina, The Journal of Microbiology, Mar. 2001, pp. 49–55, vol. 39, No. 1.

Jin–Kyoo Kim, et al., Generation and Characterization of Recombinant ScFv Antibodies Detecting Eimeria acervulina Surface Antigens, Hybridoma, vol. 20, No. 3,2001, pp. 175–181.

Wongi Min, et al., Characterization of recombinant scFv antibody reactive with an apical antigen of Eimeria acervulina, Biotechnology Letters, 23: 949–955, 2001.

* cited by examiner

Primary Examiner—Lynette R.F. Smith
Assistant Examiner—Padma Baskar
(74) Attorney, Agent, or Firm—Harness, Dickey & Pierce, P.L.C.

(57) ABSTRACT

The present invention relates to (a) variable regions of heavy and light chains of an antibody specific to a surface antigen in sporozoite of Eimeria spp.; (b) a recombinant scFV (single chain variable fragment) antibody prepared using the variable regions; (c) a method for preparing a recombinant scFv antibody; and (d) an expression vector for expressing a recombinant scFv antibody.

2 Claims, 16 Drawing Sheets

Fig. 3a

```
                  <-----------------------------------------------
GERMLINE    GCCGTGACGTTGGACGAGTCCGGGGGCGGCCTCCAGACGCCCGGAAGAGC    50
            CKVHBACK
2-1HC       .................................................G....    50
5D11HC      .................................................G....    50
13C8HC      .................................................G...G    50
8C3HC       .................................................G...G    50

GERMLINE    GCTCAGCCTCGTCTGCAAGGCCTCCGGGTTCACCTTCAGCAGTTACAACA   100
                                                    CDR1
2-1HC       .............................................CC.TGG..   100
5D11HC      ............................GA.............G...   100
13C8HC      ...............G......C..GA.............TGC..   100
8C3HC       ....................T.TA..G..G......T..   100

GERMLINE    TGGGTTGGGTGCGACAGGCGCCCGGCAAGGGGCTGGAGTTCGTCGCTGGT   150
2-1HC       ..ATG.........A.....................GG.....G...   150
5D11HC      ..AT.............................A.A.....G...   150
13C8HC      ..............,A............A......G...   150
8C3HC       ..CAC........C...A....T..A...........A.A...T..A...   150

GERMLINE    ATTGAC---AACACTGGTAGATACACAGGCTACGGGTCGGCGGTGAAGGG   197
                   CDR2
2-1HC       ...AG.---........CT.....GTA.....C.C..........   197
5D11HC      ...AGA---.GTGA......TAG..T.TA.......G.........   197
13C8HC      ...A.AAAA..TGA......T.GG...AA.....C.C..........   200
8C3HC       .....T---GCTGG....G.TAG....TA.......G........C....   197

GERMLINE    CCGTGCCACCATCTCGAGGGACAACGGGCAGAGCACAGTGAGGCTGCAGC   247
2-1HC       ..................................................   247
5D11HC      ........................................TC...........   247
13C8HC      .............................A...................   250
8C3HC       ..........G........................C...........   247

VH1 gene
GERMLINE    TGAACAACCTCAGGGCTGAGGACACCGGCACCTACTACTGCGCCAAAGCT   297
2-1HC       .................................................G.   297
5D11HC      ..........................T...........AG.   297
13C8HC      ...........C.......T...GT....A...G..A.   297
8C3HC       ..............CTG..................T.........   297

D segment              JH gene
GERMLINE    GCTGGTNNNNNNNNNNNNNNNNNNN------ACTGCTGGTAGCATCGACGC   341
                        CDR3
2-1HC       .G..C.TATTGTGCTGGT----------TG..G....GA........   335
5D11HC      T...TA.GGTAGTTGGAGAGGT---------T..A.....GA........   338
13C8HC      .T.AA.AGTGGTTACCCT----------GA.....C.GA.........   338
8C3HC       T..C.GTGTGGCTATGATTGGTGT------T......A..A..........   341

GERMLINE    ATGGGGCCACGGGACCGAAGTCATCGTCTCCTCC   375
                          CKVHFOR
2-1HC       ...............................   369
5D11HC      ...............................   372
13C8HC      ...............................   372
8C3HC       ...............................   375
```

Fig. 3b

```
                   <-----------------------------------------------
GERMLINE   GCGCTGACTCAGCCGTCCTCGGTGTCAGCGAACCCGGGAGGAACCGTCAA    50
                CKVLBACK
2-1LC      ..................A....,A....A.........          50
5D11LC     ..................A....T.....A........G.         50
13C8LC     ..................A....T..............           50
8C3LC      .........A................T........A.......G.    50

GERMLINE   GATCACCTGCTCCGGGGATAGCAGCTAC---------------TATGGCT    85
                      CDR1
2-1LC      ................G.G........GCTGGAAGTTACTAT.......  100
5D11LC     A................GC..GTATAGG-----------------...... 85
13C8LC     .................GC...TATGG.-----------------......  85
8C3LC      .................G..A..A....-----------------......  85

GERMLINE   GGTACCAGCAGAAGGCACCTGGCAGTGCCCCTGTCACTGTGATCTATGAC   135
2-1LC      ...........................C......................  150
5D11LC     ....T........T..T..................................  135
13C8LC     ....T........T................C...............CTGG  135
8C3LC      ....T........AT................................CT.. 135

GERMLINE   AACACCAACAGACCCTCGAACATCCCTTCACGATTCTCCGGTTCCAAATC   185
                CDR2
2-1LC      ...................................................CT...  200
5D11LC     ...GA...G........G.................................  185
13C8LC     ....A...G........G.................................  185
8C3LC      ....A...G........G................................C. 185

GERMLINE   CGGCTCCACAGCCACATTAACCATCACTGGGGTCCGAGCCGACGACAATG   235
2-1LC      ..........AA.......................A..T...G...G.G.  250
5D11LC     ..A......G.G.......................A......G...G.G.  235
13C8LC     ...................................G...G.G.  235
8C3LC      ..........AA.......................G...G.G.  235

Vλ 1 gene                >< 
GERMLINE   CTGTCTATTACTGTGCGAGTACAGACAGCAGCAGTACT------GCA---------------GGTATA  282
                         CDR3
2-1LC      ............G...CTTC........TTA.GT.-----------------......  294
5D11LC     ............G..A.G......A..AT.C.TAC------AT---------------CC....  282
13C8LC     ............G..A.G........---.A...------.TGATAGTGATTATGTT......  294
8C3LC      .........T.....GTGCCTGG..A..T---...C..ATTTAT.TT---------------......  285

Jλ gene        >
GERMLINE   TTTGGGGCCGGGACAACCCTGACCGTCCTA    312
                CKVLFOR
2-1LC      C............................   324
6D12LC     .............................   309
5D11LC     .............................   312
13C8LC     .............................   324
8C3LC      .............................   315
```

```
Germline    AVTLDESGGGLQTPGRALSLVCKASGFTFSSYNMGWVRQAPGKGLEFVAG      50
                                         CDR1
2-1 HC      ...............G...........HG.M....T......W...         50
5D11 HC     ...............G.........D....D.I............Y...      50
8C3 HC      ...............GG.........SIGG.I.H....T.......Y...     50
13C8 HC     ...............GG......G..LD....A.................     50

Germline    IDNT-GRYTGYGSAVKGRATISRDNGQSTVRLQLNNLRAEDTGTYYCAKA      99
                CDR2
2-1 HC      .S..-.T..Y.AP.................................-        98
5D11 HC     .RSD-.SSIY..A.....................L..............S     99
8C3 HC      ..AG-.GS.Y..A..Q....V........L........L......F....     99
13C8 HC     .KKND.SW.N.AP.........................D...I.V.TRD      100

Germline    AGXXX--XX-----XTAGSIDAWGHGTEVIVSS      124
                 CDR3
2-1 HC      -GGAY--CA-----GCG.D..............     122
5D11 HC     ---SY-----GSWRGST.D..............     123
8C3 HC      SRCGYDWCS------.DN...............     124
13C8 HC     VNSGY---------PD.AD..............     123
```

Fig. 4b

```
Germline    ALTQPSSVSANPGGTVKITCSGDSSY-----YGWYQQKAPGSAPVTVIY           44
                             CDR1

2-1  LC     ..............E........GG..AGSYY.........A........          49
5D11 LC     ............L.E..E.....-----GRYR.......SS.........          44
8C3  LC     ............I..E..E.....GNN.-----,......S..........         44
13C8 LC     ............L..........G-----SYG...F...S......P...          44

Germline    DNTNRPSNIPSRFSGSKSGSTATLTITGVRADDEAVYYCASTDSSST---           91
                CDR2                                 CDR3

2-1  LC     ....................L....N.......QVE.......G.F...YV---    94
5D11 LC     ..DK...D.........D..G......Q.E......GNA.NNTY---            91
8C3  LC     Y.NK...D.........P...N.........E.....F.GAWE..PI---         91
13C8 LC     W-NK...D........................E.......GNA..NTADSD        94

Germline    -AGIFGAGTTLTVL         104

| Antibody | FR1 | CDR1 | FR2 | CDR2 | FR3 | CDR3 |
|---|---|---|---|---|---|---|
| 5D11 | ψV4 and ψV2/7/18/23/24 | ψV14 | ψV7 | ψV7 | ψV7/12 | V12 and V11 |
| 8C3 | ψV24 | ψV23 | ψV7 | ψV12 | ψV7/10/12, ψV2/8/17, and ψV13 | ψV13 |
| 13C8 | ψV4 | ψV14 | ψV6 and ψV11 | ψV14 and ψV12/13 | ψV11 | ψV12 and ψV20 |
| 2-1 | ψV4 and ψV5/8/14 | ψV8 | ψV8 | ψV8 | ψV8 and ψV14 | ψV14 and ψV3 |

RECOMBINANT SCFV ANTIBODIES SPECIFIC TO EIMERIA SPP. RESPONSIBLE FOR COCCIDIOSIS

BACKGROUND OF THE INVENTION

1. Field of the Invention

The present invention generally relates to antibody and more particularly, relates to variable regions of heavy and light chains of an antibody specific to a surface antigen in sporozoite of Eimeria spp. and scFV (single chain variable fragment) prepared using the variable regions.

2. Description of the Related Art

Avian coccidiosis, caused by intestinal parasites belonging to genus Eimeria, is an obligate protozoan disease of chickens, resulting in a significant economic loss in the poultry industry. Despite increasing interest in developing protection strategies, the use of whole parasites or chemotherapy has major drawbacks. For example, due to the complexity of the parasite life-cycle and the existence of multiple species infecting chickens, immunity developed by using whole parasites, in general, is species-specific and cross-species protection has not been observed (Reynaud, C. A. et al., *Eur. J. Immunol.* 21:2661(1991)). The application of anti-coccidia drugs is also hindered by high costs and development of drug resistance. Therefore, research has been focused on the development of immunological controls, which is dependent on the identification and characterization of target antigens to induce protective immune responses by the host immune system.

Current efforts to develop an immunological control against coccidiosis involve identification of immunogenic epitope of Eimeria parasites to elicit cell mediated immunity (Lillehoj, H. S. et al., *Avian Dis.*, 44:408-425(2000)). In general, two immunological strategies have been envisioned. The first uses recombinant subunit vaccines derived from parasite proteins used to bind to host cell receptors since avian coccidian parasites are known to invade cells of intestinal surface epithelium (Al-Attar, M. A. et al., *J. Parasitol.*, 73:494-502(1987); and Lawn, A. M. et al., *J. Parasitol.*, 68:1117-1123 (1982)). The second approach involves passive immunization with antibodies that actively block the interaction of parasites with host cells (Sasaki, K. et al., *J. Parasitol.*, 82:82-87(1996)).

Many coccidial antigens have been identified with mouse antibodies (Speer, C. A. et al., *J. Protozol.*, 30:548-554 (1983)), and their cDNAs have been cloned for the development of a subunit vaccine (Castle, M. D. et al., *J. Parasitol.*, 77:384-390(1991); and Ko, C. et al., *Mol. Bio. Parasitol.*, 73:790-792 (1993)). However, the efficacy of these antibodies is debatable (Trout, J. et al., *J. Parasitol.*, 73:790-792(1993)), because of differences in the target antigens recognized by immune sera from chickens and mice (Jenkins, M. C. et al., *Mol. Bio. Parasitol.*, 25:155-164(1987)).

Therefore, in this regard, chicken antibodies may be more advantageous for the identification of target antigens to cause avian coccidiosis.

Recently, the present inventors have been developed four chicken monoclonal antibodies (Mabs: 2-1, 5D11, 8C3 and 13C8) which recognize Eimeria antigens (Lillehoj, H. S. et al., *Eimeria. Poul. Sci.*, 73:1685-1693(1994) and Lillehoj, H. S. et al., *J. Parasitol.*, 82:82-87(1996)), and characterized their biochemical properties. The immunologic nature of antigens recognized by these antibodies is under the investigation. Recently, the present inventors found that the developed chicken Mabs (monoclonal antibodies) recognize the surface antigens localized in the apical complex of *Eimeria acervulina*. This promising result suggests the possible application of anti-Eimeria Mabs for passive immunization. However, chicken hybridomas have some drawbacks such as production of a low amount of antibody and of non-specific IgM, and the loss of ability to produce antibodies (Nishinaka, S. et al., *J. Immunol. Methods.*, 139:217-222(1991); and Nishinaka, S. et al., *J. Vet. Med. Sci.*, 58:1053-1056(1996)).

U.S. Pat. No. 4,710,377 discloses monoclonal antibodies against sporozoites of he Eimeria spp. obtained by use of hybridoma technology, and U.S. Pat. No. discloses novel recombinant antigenic proteins of avian coccidiosis, and fragments thereof containing antigenic determinants.

Moreover, U.S. Pat. No. 5,635,181 discloses anti-coccidial vaccine containing a recombinant peptide with novel epitopes and U.S. Pat. No. 4,301,148 discloses a method for preventing fowl coccidiosis comprising inoculating newly hatched fowl with sporozoites of Eimeria.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

In one aspect of this invention, there is provided a heavy chain variable region of an antibody specific to a surface antigen in sporozoite of Eimeria spp., which comprises an amino acid sequence selected from the group consisting of SEQ ID NO: 18, SEQ ID NO: 20, SEQ ID NO: 22, SEQ ID NO: 24 and SEQ ID NO: 38.

In another aspect of this invention, there is provided a light chain variable region of an antibody specific to a surface antigen in sporozoite of Eimeria spp., which comprises an amino acid sequence selected from the group consisting of SEQ ID NO: 26, SEQ ID NO: 28, SEQ ID NO: 30, SEQ ID NO: 32 and SEQ ID NO: 40.

In still another aspect of this invention, there is provided a DNA molecule encoding a heavy chain variable region of an antibody specific to a surface antigen in sporozoite of Eimeria spp., wherein the heavy chain variable region comprises an amino acid sequence selected from the group consisting of SEQ ID NO: 18, SEQ ID NO: 20, SEQ ID NO: 22, SEQ ID NO: 24 and SEQ ID NO: 38.

In further aspect of this invention, there is provided a DNA molecule encoding a light chain variable region of an antibody specific to a surface antigen in sporozoite of Eimeria spp., wherein the light chain variable region comprises an amino acid sequence selected from the group consisting of SEQ ID NO: 26, SEQ ID NO: 28, SEQ ID NO: 30, SEQ ID NO: 32 and SEQ ID NO: 40.

In still further aspect of this invention, there is provided a recombinant scFv (single chain variable fragment) antibody specific to a surface antigen in sporozoite of Eimeria spp., which comprises: (a) a heavy chain variable region of an antibody specific to a surface antigen in sporozoite of Eimeria spp., comprising an amino acid sequence selected from the group consisting of SEQ ID NO: 18, SEQ ID NO: 20, SEQ ID NO: 22, SEQ ID NO: 24 and SEQ ID NO: 38; and (b) a light chain variable region of an antibody specific to a surface antigen in sporozoite of Eimeria spp., comprising an amino acid sequence selected from the group consisting of SEQ ID NO: 26, SEQ ID NO: 28, SEQ ID NO: 30, SEQ ID NO: 32 and SEQ ID NO: 40.

In another aspect of this invention, there is provided a DNA molecule encoding scFv antibody specific to a surface antigen in sporozoite of Eimeria spp., which comprises: (a) a DNA molecule encoding a heavy chain variable region of an antibody specific to a surface antigen in sporozoite of Eimeria spp., wherein the heavy chain variable region comprises an amino acid sequence selected from the group consisting of SEQ ID NO: 18, SEQ ID NO: 20, SEQ ID NO: 22, SEQ ID NO: 24 and SEQ ID NO: 38; and (b) a DNA molecule encoding a light chain variable region of an antibody specific to a surface antigen in sporozoite of Eimeria spp., wherein the light chain variable region comprises an amino acid sequence selected from the group consisting of SEQ ID NO: 26, SEQ ID NO: 28, SEQ ID NO: 30, SEQ ID NO: 32 and SEQ ID NO: 40.

In still another aspect of this invention, there is provided a method for preparing a recombinant scFv antibody specific to a surface antigen in sporozoite of Eimeria spp., which comprises: (a) cloning an scFv gene construct comprising (i) a DNA molecule encoding a heavy chain variable region of an antibody specific to a surface antigen in sporozoite of Eimeria spp., wherein the heavy chain variable region comprises an amino acid sequence selected from the group consisting of SEQ ID NO: 18, SEQ ID NO: 20, SEQ ID NO: 22, SEQ ID NO: 24 and SEQ ID NO: 38; and (ii) a DNA molecule encoding a light chain variable region of an antibody specific to a surface antigen in sporozoite of Eimeria spp., wherein the light chain variable region comprises an amino acid sequence selected from the group consisting of SEQ ID NO: 26, SEQ ID NO: 28, SEQ ID NO: 30, SEQ ID NO: 32 and SEQ ID NO: 40 into an expression vector; (b) transforming host cells with the expression vector of (a); and (c) expressing and isolating the recombinant scFv antibody in host cells.

In further aspect of this invention, there is provided an expression vector for expressing a recombinant scFv antibody specific to a surface antigen in sporozoite of Eimeria spp., which comprises: (a) an scFv gene construct comprising (i) a DNA molecule encoding a heavy chain variable region of an antibody specific to a surface antigen in sporozoite of Eimeria spp., wherein the heavy chain variable region comprises an amino acid sequence selected from the group consisting of SEQ ID NO: 18, SEQ ID NO: 20, SEQ ID NO: 22, SEQ ID NO: 24 and SEQ ID NO: 38; and (ii) a DNA molecule encoding a light chain variable region of an antibody specific to a surface antigen in sporozoite of Eimeria spp., wherein the light chain variable region comprises an amino acid sequence selected from the group consisting of SEQ ID NO: 26, SEQ ID NO: 28, SEQ ID NO: 30, SEQ ID NO: 32 and SEQ ID NO: 40 into an expression vector; and (b) a promoter controlling an expression of scFv gene construct.

Accordingly, it is an object of this invention to provide a heavy chain variable region of an antibody specific to a surface antigen in sporozoite of Eimeria spp.

It is another object of this invention to provide a light chain variable region of an antibody specific to a surface antigen in sporozoite of Eimeria spp.

It is still another object of this invention to provide a DNA molecule encoding a heavy chain variable region of an antibody specific to a surface antigen in sporozoite of Eimeria spp.

It is further object of this invention to provide a DNA molecule encoding a light chain variable region of an antibody specific to a surface antigen in sporozoite of Eimeria spp.

It is still further object of this invention to provide a recombinant scFv antibody specific to a surface antigen in sporozoite of Eimeria spp.

It is another object of this invention to provide a DNA molecule encoding scFv antibody specific to a surface antigen in sporozoite of Eimeria spp.

It is still another object of this invention to provide a method for preparing a recombinant scFv antibody specific to a surface antigen in sporozoite of Eimeria spp.

It is further object of this invention to provide an expression vector for expressing a recombinant scFv antibody specific to a surface antigen in sporozoite of Eimeria spp.

Other objects and advantages of the present invention will become apparent from the detailed description to follow taken in conjugation with the appended claims and drawings.

BRIEF DESCRIPTION OF THE DRAWINGS

FIG. 3a represents sequence homology between nucleotide sequences of heavy chain of anti-Eimeria monoclonal antibodies and germline sequences;

FIG. 3b represents sequence homology between nucleotide sequences of light chain of anti-Eimeria monoclonal antibodies and germline sequences;

FIG. 3c represents sequence homology between nucleotide sequences of heavy chain of antii-Eimeria monoclonal antibodies derived from 6D-12-G10 hybridoma and germline sequences;

FIG. 3d represents sequence homology between nucleotide sequences of light chain of anti-Eimeria monoclonal antibodies derived from 6D-12-G10 hybridoma and germline sequences;

FIG. 4a represents sequence homology of amino acid sequences deduced from sequences of FIG. 3a;

FIG. 4b represents sequence homology of amino acid sequences deduced from sequences of FIG. 3b;

FIG. 5 shows gene conversion of pseudogene sequences accounted by nucleotide sequence of this invention encoding anti-coccidiosis antibody;

DETAILED DESCRIPTION OF THIS INVENTION

Figure 1:
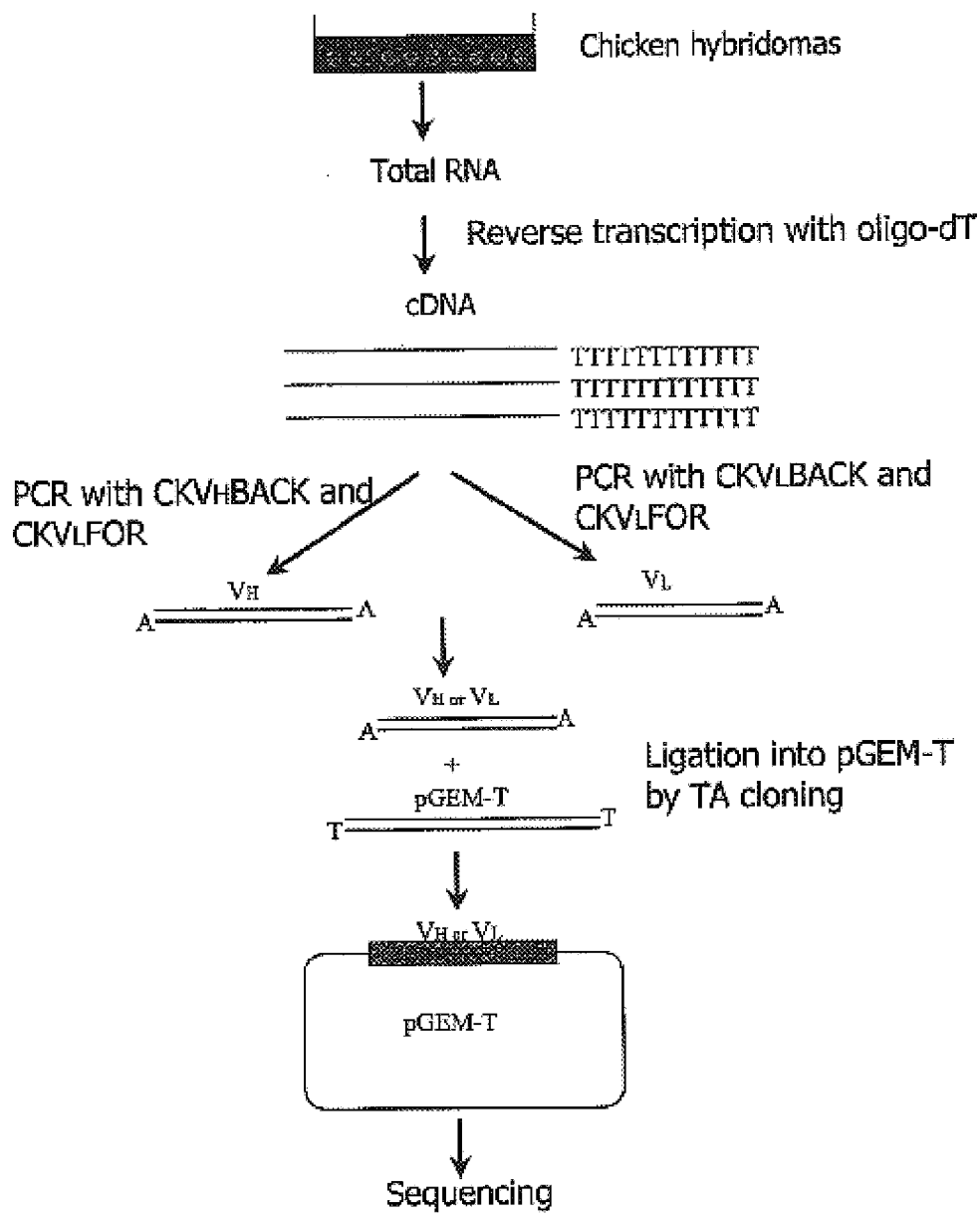
FIG. 1 represents cloning strategy of variable regions from chicken hybridomas secreting Eimeria antigen specific monoclonal antibodies.

The present invention has been developed in order to be free from some shortcomings of conventional techniques aforementioned, particularly, method for preparing anticoccidial antibody using hybridoma cells. The present inventors employ recombinant antibody method to overcome drawbacks of method using hybridoma cells, adopting binding characteristics of antibody that antigen binding domain, i.e., variable region of heavy and light chains (λ or κ) is necessarily required for antigen-antibody binding to exhibit an inherent function of antibody. Therefore, the present invention provides a heavy chain variable region of an antibody specific to a surface antigen in sporozoite of Eimeria spp.

The present DNA molecules encoding heavy and light chains variable regions of antibodies specific to a surface antigen in sporozoite of Eimeria spp. can be obtained in accordance with the following strategy. Unlike mammals such as mice and humans, the immunoglobulin gene diversification in chicken is mainly constructed by gene conversion (Renaud, C. A. et al., *Cell,* 40:283-291(1985); Reyanud, C. A. et al., *Cell,* 48:379-388(1987); Reyanud, C. A. et al., *Cell,* 59:171-183(1989); and Rose, M. E., *Immune reponse in parasitic Infections; Immunology, Immunopathology, Immunoprophylaxis,* CRC Press, Boca Raton, Fla., p.275 (1987)). More particularly, single functional immunoglobulin variable and joining segments at each of the heavy and λ-light chain loci are diversified by conversions with upstream pseudo variable region genes as sequence donors (Reyanud, C. A. et al., *Cell,* 48:379-388(1987); Reyanud, C. A. et al., *Cell,* 59:171-183(1989); Rose, M. E., *Immune reponse in parasitic Infections; Immunology, Immunopathology, Immunoprophylaxis,* CRC Press, Boca Raton, Fla., p.275(1987); and Thompson, C. B. et al., *Cell,* 48:369-378(1987)). Since the sequences of pseudogenes are highly conserved in the 5'-and 3'-flanking region suggesting that all variable regions in mature B cells or hybridoma have identical ends, gene conversions in chickens make it possible to amplify variable region genes using a single pair of primers per heavy and λ-light chains.

The amplification of the present genes can be performed by PCR method (Saiki, R. K., *PCR Technology, Principles and Applications for DNA Amplification,* Erlich, H. A. ed., Stockton Press, New York(1989)). The primers used in this invention are designed based on conservation in flanking region sequence of pseudogene. The primer for amplifying variable region of heavy chain, preferably, is a single pair of DNA molecules encoding amino acids of SEQ ID NO: 33 and SEQ ID NO: 34 and more preferably, a single pair of primers of SEQ ID NO: 1 or its complementary sequence and SEQ ID NO: 2 or its complementary sequence.

The primer for amplifying variable region of light chain, preferably, is a single pair of DNA molecules encoding amino acids of SEQ ID NO: 35 and SEQ ID NO: 36 and more preferably, a single pair of primers of SEQ ID NO: 3 or its complementary sequence and SEQ ID NO: 4 or its complementary sequence.

According to preferred embodiment of this invention, the DNA molecule encoding a heavy chain variable region of an antibody specific to a surface antigen in sporozoite of Eimeria spp. comprises a nucleotide sequence selected from the group consisting of SEQ ID NO: 17, SEQ ID NO: 19, SEQ ID NO: 21, SEQ ID NO: 23 and SEQ ID NO: 37.

According to preferred embodiment of this invention, the DNA molecule encoding a light chain variable region of an antibody specific to a surface antigen in sporozoite of Eimeria spp. , comprises a nucleotide sequence selected from the group consisting of SEQ ID NO: 25, SEQ ID NO: 27, SEQ ID NO: 29, SEQ ID NO: 31 and SEQ ID NO: 39.

The DNA molecules of this invention as described herein, are considered to include some variations. For example, as a result of the degeneracy of the genetic code (Crick, F. H. et al., *Nature,* 192:1227(1961)), a multitude of variable regions-encoding nucleotide sequences may be prepared. These variations are made in accordance with the standard triplet genetic code and it is understood that all such variations fall within the scope of this invention. Moreover, the DNA molecules of this invention include those with nucleotide sequence showing at least 60% sequence identity (more preferably, at least 75% identity; most preferably, at least 90% or 95% identity), when compared and aligned for maximum correspondence. The DNA molecules of this invention also encompass those with sequences complementary thereto. This invention also includes the DNA molecules capable of hybridizing under reduced stringency conditions, more preferably stringent conditions, and most preferably highly stringent conditions, to the DNA molecules specifically described herein.

The variable regions of heavy and light chains of this invention as described herein, are considered to include some variations and modifications. The variable regions of this invention include the polypeptides with amino acid sequence showing at least 60% sequence identity (more preferably, at least 75% identity; most preferably, at least 90% or 95% identity) when compared and aligned for maximum correspondence, if exhibiting antigen-binding capacity substantially.

Using the amino acid sequences and the DNA molecule elucidated in this invention, a recombinant antibody such as scFv (single chain variable fragments) can be prepared. Therefore, the present invention is directed to a recombinant scFv antibody specific to a surface antigen in sporozoite of Eimeria spp.

According to preferred embodiment of the scFv antibody, the heavy chain variable region comprises the amino acid sequence of SEQ ID NO: 18 and the light chain variable region comprises the amino acid sequence of SEQ ID NO: 26.

According to preferred embodiment of this invention, the heavy chain variable region comprises the amino acid sequence of SEQ ID NO: 20 and the light chain variable region comprises the amino acid sequence of SEQ ID NO: 28.

According to preferred embodiment of this invention, the heavy chain variable region comprises the amino acid sequence of SEQ ID NO: 22 and the light chain variable region comprises the amino acid sequence of SEQ ID NO: 30.

According to preferred embodiment of this invention, the heavy chain variable region comprises the amino acid sequence of SEQ ID NO: 24 and the light chain variable region comprises the amino acid sequence of SEQ ID NO: 32.

In the scFv antibody, preferably, the heavy chain variable region comprises the amino acid sequence of SEQ ID NO: 38 and the light chain variable region comprises the amino acid sequence of SEQ ID NO: 40.

Alternatively, the scFv antibody of this invention further comprises a linker between the heavy chain variable region and the light chain variable region. The linker is a peptide molecule that link variable regions of heavy and light chains to stabilize antigen-binding capacity of the resulting scFv antibody (for exampler, GS linker: Huston, et al., *Methods in Enzymology,* 203:46-88(1991); and EK linker: Whitlow, et al., *Protein Eng.,* 6:989(1993)). The linker mainly comprises glycine and serine residues and is 15-18 amino acids in length. Therefore, in the scFv antibody of this invention, the most preferable combination is: (a) heavy chain variable region of SEQ ID NO: 18-linker-light chain variable region of SEQ ID NO: 26; (b) heavy chain variable region of SEQ ID NO: 20-linker-light chain variable region of SEQ ID NO: 28; (c) heavy chain variable region of SEQ ID NO: 22-linker-light chain variable region of SEQ ID NO: 30; (d) heavy chain variable region of SEQ ID NO: 24-linker-light chain variable region of SEQ ID NO: 32; and (e) heavy chain variable region of SEQ ID NO: 38-linker-light chain variable region of SEQ ID NO: 40.

The present invention is also directed to a DNA molecule encoding scFv antibody specific to a surface antigen in sporozoite of Eimeria spp.

According to preferred embodiment of the DNA molecule encoding scFv antibody, the DNA molecule encoding a heavy chain variable region comprises DNA molecule encoding the amino acid sequence of SEQ ID NO: 18 and the DNA molecule encoding a light chain variable region comprises DNA molecule encoding the amino acid sequence of SEQ ID NO: 26.

According to preferred embodiment of the DNA molecule encoding scFv antibody, the DNA molecule encoding a heavy chain variable region comprises DNA molecule encoding the amino acid sequence of SEQ ID NO: 20 and the DNA molecule encoding a light chain variable region comprises DNA molecule encoding the amino acid sequence of SEQ ID NO: 28.

According to preferred embodiment of the DNA molecule encoding scFv antibody, the DNA molecule encoding a heavy chain variable region comprises DNA molecule encoding the amino acid sequence of SEQ ID NO: 22 and the DNA molecule encoding a light chain variable region comprises DNA molecule encoding the amino acid sequence of SEQ ID NO: 30.

According to preferred embodiment of the DNA molecule encoding scFv antibody, the DNA molecule encoding a heavy chain variable region comprises DNA molecule encoding the amino acid sequence of SEQ ID NO: 24 and the DNA molecule encoding a light chain variable region comprises DNA molecule encoding the amino acid sequence of SEQ ID NO: 32.

According to preferred embodiment of the DNA molecule encoding scFv antibody, the DNA molecule encoding a heavy chain variable region comprises DNA molecule encoding the amino acid sequence of SEQ ID NO: 38 and the DNA molecule encoding a light chain variable region comprises DNA molecule encoding the amino acid sequence of SEQ ID NO: 40.

According to preferred embodiment of the DNA molecule encoding scFv antibody, the DNA molecule encoding scFv antibody further comprises a DNA molecule encoding linker between the DNA molecule encoding the heavy chain variable region and the DNA molecule encoding the light chain variable region.

According to more preferred embodiment of the DNA molecule encoding scFv antibody, the DNA molecule encoding the heavy chain variable region comprising the amino acid sequence of SEQ ID NO: 18 comprises DNA molecule of SEQ ID NO: 17, the DNA molecule encoding the heavy chain variable region comprising the amino acid sequence of SEQ ID NO: 20 comprises DNA molecule of SEQ ID NO: 19, the DNA molecule encoding the heavy chain variable region comprising the amino acid sequence of SEQ ID NO: 22 comprises DNA molecule of SEQ ID NO: 21, the DNA molecule encoding the heavy chain variable region comprising the amino acid sequence of SEQ ID NO: 24 comprises DNA molecule of SEQ ID NO: 23, and the DNA molecule encoding the heavy chain variable region comprising the amino acid sequence of SEQ ID NO: 38 comprises DNA molecule of SEQ ID NO: 37.

According to more preferred embodiment of the DNA molecule encoding scFv antibody, the DNA molecule encoding the light chain variable region comprising the amino acid sequence of SEQ ID NO: 26 comprises DNA molecule of SEQ ID NO: 25, the DNA molecule encoding the light chain variable region comprising the amino acid sequence of SEQ ID NO: 28 comprises DNA molecule of SEQ ID NO: 27, the DNA molecule encoding the light chain variable region comprising the amino acid sequence of SEQ ID NO: 30 comprises DNA molecule of SEQ ID NO: 29, the DNA molecule encoding the light chain variable region comprising the amino acid sequence of SEQ ID NO: 32 comprises DNA molecule of SEQ ID NO: 31, the DNA molecule encoding the light chain variable region comprising the amino acid sequence of SEQ ID NO: 40 comprises DNA molecule of SEQ ID NO: 39.

The application of scFv antibody of this invention includes fowl susceptible to avian coccidosis, for example, chicken, duck, turkey, quail, pheasant, ostrich and goose.

Eimeria spp. influenced by scFv antibody of this invention includes a variety of Eimeria causing avian coccidiosis, for example, *Eimeria acervulina, Eimeria tenella, Eimeria maxima, Eimeria coccidia, Eimeria mitis, Eimeria praecox, Eimeria brunetti, Eimeria necatrix, Eimeria mivati* and *Eimeria hagani.*

Eimeria spp. has a complicated life cycle consisting of both asexual and sexual stages. Invasive asexual sporozoites are developed in the host's digestive track and then developed multinucleate structures known as shizonts. Therefore, the present scFv antibody specific to a surface antigen in sporozoite of Eimeria spp. is very effective in protection to infection of the parasites.

By means of the DNA molecule encoding variable regions of heavy and light chains of this invention, a recombinant scFv antibody is massively prepared in suitable host cells. The present invention, therefore, is directed a method for preparing a recombinant scFv antibody specific to a surface antigen in sporozoite of Eimeria spp.

In the preparing method of this invention, the host cells include those used conventionally for expression of expression vector, comprising both eukaryotic and prokaryotic cells. Preferably, the host cells are prokaryotic cells. In consideration of commercial availability, *E. coli* such as BMH71-18 or BL 21(DE) strains or Bacillus spp. is more preferable.

According to preferred embodiment of this method, the scFv gene construct comprises the DNA molecule encoding scFv antibody having a heavy chain variable region comprising the DNA molecule encoding the amino acid sequence of SEQ ID NO: 18 and a light chain variable region comprising the DNA molecule encoding the amino acid sequence of SEQ ID NO: 26.

According to preferred embodiment of this method, the scFv gene construct comprises the DNA molecule encoding scFv antibody having a heavy chain variable region comprising the DNA molecule encoding the amino acid sequence of SEQ ID NO: 20 and a light chain variable region comprising the DNA molecule encoding the amino acid sequence of SEQ ID NO: 28.

According to preferred embodiment of this method, the scFv gene construct comprises the DNA molecule encoding scFv antibody having a heavy chain variable region comprising the DNA molecule encoding the amino acid sequence of SEQ ID NO: 22 and a light chain variable region comprising the DNA molecule encoding the amino acid sequence of SEQ ID NO: 30.

According to preferred embodiment of this method, the scFv gene construct comprises the DNA molecule encoding scFv antibody having a heavy chain variable region comprising the DNA molecule encoding the amino acid sequence of SEQ ID NO: 24 and a light chain variable region comprising the DNA molecule encoding the amino acid sequence of SEQ ID NO: 32.

According to preferred embodiment of this method, the scFv gene construct comprises the DNA molecule encoding scFv antibody having a heavy chain variable region comprising the DNA molecule encoding the amino acid sequence of SEQ ID NO: 38 and a light chain variable region comprising the DNA molecule encoding the amino acid sequence of SEQ ID NO: 40.

Alternatively, in this method, the scFv gene construct further comprises a DNA molecule encoding linker between the DNA molecule encoding the heavy chain variable region and the DNA molecule encoding the light chain variable region. Insertion of the linker sequence can be performed according to a variety of methods known to one skilled in the art, including overlap-extension PCR (Horton, R. M. et al., *Gene,* 77:61-68(1989)) during construction of scFv gene construct exemplified in examples below.

According to more preferred embodiment of this method, the DNA molecule encoding the heavy chain variable region comprising the amino acid sequence of SEQ ID NO: 18 comprises DNA molecule of SEQ ID NO: 17, the DNA molecule encoding the heavy chain variable region comprising the amino acid sequence of SEQ ID NO: 20 comprises DNA molecule of SEQ ID NO: 19, the DNA molecule encoding the heavy chain variable region comprising the amino acid sequence of SEQ ID NO: 22 comprises DNA molecule of SEQ ID NO: 21, the DNA molecule encoding the heavy chain variable region comprising the amino acid sequence of SEQ ID NO: 24 comprises DNA molecule of SEQ ID NO: 23, and the DNA molecule encoding the heavy chain variable region comprising the amino acid sequence of SEQ ID NO: 38 comprises DNA molecule of SEQ ID NO: 37.

According to more preferred embodiment of this method, the DNA molecule encoding the light chain variable region comprising the amino acid sequence of SEQ ID NO: 26 comprises DNA molecule of SEQ ID NO: 25, the DNA molecule encoding the light chain variable region comprising the amino acid sequence of SEQ ID NO: 28 comprises DNA molecule of SEQ ID NO: 27, the DNA molecule encoding the light chain variable region comprising the amino acid sequence of SEQ ID NO: 30 comprises DNA molecule of SEQ ID NO: 29, the DNA molecule encoding the light chain variable region comprising the amino acid sequence of SEQ ID NO: 32 comprises DNA molecule of SEQ ID NO: 31, the DNA molecule encoding the light chain variable region comprising the amino acid sequence of SEQ ID NO: 40 comprises DNA molecule of SEQ ID NO: 39.

In the present method, the step of transforming can be carried out by a large number of methods known to one skilled in the art. For example, in case of prokaryotic cells as host, $CaCl_2$ method (Cohen, S. N. et al., *Proc. Natl. Acac. Sci. U.S.A.,* 9:2110-2114(1973)), Hanahan method (Cohen, S. N. et al., *Proc. Natl. Acac. Sci. U.S.A.,* 9:2110-2114 (1973); and Hanahan, D., *J. Mol. Biol.,* 166:557-580(1983)) and electrophoresis (Dower, W. J. et al., *Nucleic. Acids Res.,* 16:6127-6145(1988)) can be used for transformation. Also, in case of eukaryotic cells as host, microinjection (Capecchi, M. R., *Cell,* 22:479(1980)), calcium phosphate precipitation (Graham, F. L. et al., *Virology,* 52:456(1973)), electrophoresis (Neumann, E. et al., *EMBO J.,* 1:841(1982)), liposome-mediated transfection (Wong, T. K. et al., *Gene,* 10:87 (1980)), DEAE-dextran treatment (Gopal, *Mol. Cell Biol.,* 5:1188-1190(1985)), and particle bombardment (Yang et al., *Proc. Natl. Acad. Sci.,* 87:9568-9572(1990)) can be use for transformation.

Expression vectors in host cells express scFv antibodies of interest. According to preferred embodiment of this method, if expression vector carries lac promoter, the induction of expression can be performed using IPTG (isopropyl-β-D-thiogalactopyranoside).

The present invention is directed to an expression vector used for the method described above.

The common descriptions of both preparing method and expression vector of this invention are abbreviated in order to avoid the complexity of this specification leading to undue multiplicity. For example, descriptions for scFv gene construct, DNA molecules encoding variable regions of heavy and light chains employed and linker are substantially identical in both preparing method and expression vector of this invention.

According to preferred embodiment of this vecor, the vector further comprises a DNA molecule encoding a leader sequence located upstream of the scFv gene construct facilitating extracellular secretion of scFv antibody. Non-limiting examples of leader sequence include pel B, gene III and ompA leader sequence.

Alternatively, the expression vector of this invention further comprises fusion sequence located downstream of the scFv gene construct so that purification of scFv expressed may be successfully accomplished with improved feasibility and yield. The term used herein "fusion sequence" refers to an additional sequence fused to the sequence of interest in order to facilitate purification.

The fusion sequence includes, but not limited to, glutathione S-transferase (Pharmacia, USA), maltose binding protein (NEB, USA), FLAG (IBI, USA) and 6X His (hexahistidine; Quiagen, USA). The most preferable sequence is 6X His because it has not antigenicity and does not interfere desirable folding of fused protein, i.e., variable regions of heavy and light chains. Due to the fusion sequence, the protein expressed can be purified with affinity chromatography in a rapid and feasible manner.

According to preferred embodiment of this invention, the fusion protein is purified by affinity chromatography. For example, in case of using glutathione S-transferase, elution buffer containing glutathione is employed and in case of using 6X His, Ni-NTA His-binding resin (Novagen, USA) is generally employed to purify scFv antibody of interest in a rapid and feasible manner.

If the expression vector for scFv antibody of this invention uses prokaryotic cells as expression host, it is preferred that the vector carries any strong promoter such as $P_L^{80}$ promoter, trp promoter, lac promoter and T7 promoter. If the expression vector uses eukaryotic cells as expression host, it is preferred that the vector carries promoter derived from the genome of mammalian cells (e.g., metallothionein promoter) or from mammalian viruses (e.g., adenovirus late promoter; vaccinia virus 7.5K promoter, SC 40 promoter, cytomegalovirus promoter and tk promoter of HSV).

It is preferable that the expression of this invention carries antibiotics-resistance gene commonly used in this art, including resistance genes to ampicillin, gentamycine, chloramphenicol, streptomycin, kanamycin, neomycin or tetracycline. In light of cost, resistance genes to ampicillin or gentamycine are more preferable.

The following specific examples are intended to be illustrative of the invention and should not be construed as limiting the scope of the invention as defined by appended claims.

EXAMPLES

Materials and Methods

I. Chickens

Embryonated eggs of White Leghorn crosses ($SC^R$) obtained as fertile eggs from a commercial breeder (Hyline International, Dallas Center, Iowa, U.S.A.) were hatched at the Parasite Immunobiology Laboratory, Beltsville, Md., and maintained in brooders until 3 weeks of age, at which time they were kept in wire colony cages. Chickens were housed in clean wire-floored cages. Special care was taken not to expose the chickens to specific pathogens. Food and water were available ad libitum.

II. Preparation of *Eimeria acervulina* Sporozoites

Sporulated oocysts of *E. acervulina* (#34 USDA strain, U.S.A.) were collected. Sporozoites were prepared by excysting *E. acervulina* oocysts in a solution containing 0.125% (w/v) trypsin (Sigma, U.S.A.) and 1% taurodeoxycholic acid in Hank's balanced salt solution (HBSS), pH 7.6 for 10 min at 41° C. in a 5% $CO_2$ incubator. Sporozoites were separated from cellular debris on DEAE-cellulose columns (DE52; Whatman Paper Ltd. U.S.A.).

III. Preparation of Sporozoite Antigens

Pelleted sporozoites ($10^9$/ml) in phosphate-buffered saline (PBS) were freeze-thawed 6 times with dry ice and warmed to room temperature, then sonicated at 40° C. with a Microson Ultrasonic Cell Disrupter (Heat System, U.S.A.).

IV. Development of Chicken B-cell Hybridoma

IV-1. Preparation of Hybridoma Cell Lines 2-1, 5D11, 8C3 and 13C8

To produce hybridomas that produce Mabs (monoclonal antibodies) specific to coccidial antigens, 6-12-wk-old SC chickens were intramuscularly injected with soluble antigen prepared from *E. acervulina* sporozoites which was emulsified in Freund's complete adjuvant. A second injection with the same preparation was given in Freund's incomplete adjuvant and additional immunizations were given by intravenous injection with the same preparation without adjuvant at 1-wk intervals. A final boost was given intravenously 3 days before fusion. Spleens from these chickens were used for hybridization.

Production of hybridomas was carried out as described by Nishinaka et al. (*J. Immunol. Methods.,* 139:217-222(1991); and *J. Vet. Med. Sci.,* 58:1053-1056(1996)) Briefly, 3 days after the last immunization, single cell suspensions of spleens were prepared by centrifugation for 20 min at 500 g on a Ficoll-Paque density gradient at 20° C. The cell fusion was carried out as described in Lillehoj, H. S. et al., *Poul. Sci.,* 73:1685-1693(1994)), using the R27H4 nonsecreting chicken myeloma cell line (obtained from Dr. Nishinaka S. in Biotechnology Development Center, NKK Corporation, Japan) in polyethylene glycol 4000 (Sigma, U.S.A.). The fused cells were suspended in Iscove's modified Dulbecco's medium (IMDM) supplemented with 10% fetal calf serum (FCS) and hypoxanthine-aminopterin-thymidine (HAT; Sigma) and plated in 96-well microculture plates. After 2 weeks, culture supernatants from hybrid clones were screened using an enzyme-linked immunosorbent assay (ELISA; Langone, J. J. et al., *Immunochemical Techniques,* Part A. Methods in Enzymology, 92, Academic Press (1983)) with sporozoite antigens on a solid phase. Hybridomas secreting the Mabs of interest were cloned by limiting dilution using irradiated spleen cells ($2 \times 10^6$ per well) as feeder cells. Several types of hybridomas obtained thus were referred to as "2-1", "5D11", "C3" and "13C8", respectively. Classification of hybridomas were made with consideration of the differences of: (a) antibody subtype secreted; (b) antibody secretion rate and productivity; (c) antigen binding capacity; and (d) epitope in antigen recognized by monoclonal antibody.

Undiluted cultural supernatant from hybridoma was used in all experiments.

IV-2. Preparation of Hybridoma Cell Line 6D-12-G10

(1) Preparation of $CD8^+$ T Cells

Spleens were obtained from 6- to 8-week-old SC chickens and macerated with a syringe plunger through a screen sieve in HBSS. The single cell suspension was overlayered onto Histopaque 1077 density gradient medium (Sigma, U.S.A.) and centrifuged at 1,800 rpm for 20 min at room temperature. Lymphocytes at the interface were removed with a Pasteur pipet and washed 3 times in HBSS. Production of $CD8^+$ T cell hybridomas was carried out by fusing spleen lymphocytes with R1/5 chicken T lymphoma cells (obtained from Dr. Lillehoj, Parasite Biology, Epidemiology, Systemic Laboratory, Animal and Natural Resources Institute, U.S.A.) in polyethyleneglycol 4,000. The hybridomas were resuspended in Iscove's modified Dulbecco's medium supplemented with 10% fetal calf serum, and hypoxanthine-aminopterin-thymidine (HAT; Sigma), and plated in U-buttom 96-well microculture plates. When hybridomas showed confluency, half of the cells from positive wells were analyzed by flow cytometry with a monoclonal antibody detecting the CD8 antigen as described (Lillehoj et al., *Eur. J. Immun.* 18:2059-2065(1988)). The stained cells were analyzed using an EPICS Profile II flow cytometer (Coulter Cooperation, Hialeah, Fla., U.S.A.). For each hybridoma, $10^4$ viable cells were analyzed. $CD8^+$ T cell hybridomas were cloned by limiting dilution using irradiated spleen cells ($2 \times 10^6$ per well) as feeder cells (see Lillehoj et al., *Eur. J. Immun.* 18:2059-2065(1988)). Hybridomas expressing the CD8 antigen were grown and aliquots frozen for use.

(2) Development of Hybridoma 6D-12-G10

To produce hybridomas that produce Mabs (monoclonal antibodies) which identify coccidial antigens with binding specificity for $CD8^+$ lymphocytes, 6-12-week-old SC chickens were intramuscularly injected with $10^8$ $CD8^+$ T cells preadsorbed with soluble antigen prepared from *E. acervulina* sporozoites ($10^7$). Preadsorption was carried out by incubating $CD8^+$ lymphocytes with soluble sporozoite antigen in 1 ml of IMDM supplemented with 10% FCS for 2 hr at 37° C. with agitation. After washing 3 times, $10^8$ $CD8^+$ T cells were resuspended in 0.5 ml of HBSS, emulsified in 0.5 ml of Freund's complete adjuvant, and injected intramuscularly into 6-12-week-old SC chickens. A second injection with the same preparation was given in Freund's incomplete adjuvant and additional immunizations were given by intravenous injection with the same preparation without adjuvant at 1-wk intervals. A final boost was given intravenously 3 days before fusion and spleens from these chickens were used for hybridization.

Production of hybridomas was carried out as described by Nishinaka et al. (*J. Immunol. Methods.,* 139:217-222(1991); and *J. Vet. Med. Sci.,* 58:1053-1056(1996)). Briefly, 3 days after the last immunization, single cell suspensions of spleens were prepared by centrifugation for 20 min at 500 g on a Ficoll-Paque density gradient at 20° C. The cell fusion was carried out as described in Lillehoj, H. S. et al., *Poul. Sci.*, 73:1685-1693(1994)), using the R27H4 nonsecreting chicken myeloma cell line (obtained from Dr. Nishinaka S. in Biotechnology Development Center, NKK Corporation, Japan) in polyethylene glycol 4000 (Sigma, U.S.A.). The fused cells were suspended in IMDM supplemented with 10% fetal calf serum (FCS) and HAT and plated in 96-well microculture plates. After 2 weeks, culture supernatants from hybrid clones were screened using ELISA with sporozoite antigens on a solid phase. Hybridomas secreting the Mabs of interest were cloned by limiting dilution using irradiated spleen cells ($2\times10^6$ per well) as feeder cells. The hybridoma obtained thus was referred to as "6D-12-G10".

V. Isolation and Amplification of Heavy and λ-Light Chain Variable Domain Genes

Total RNA was purified from hybridoma cell lines, 2-1, 5D11, 8C3, 13C8 and 6D-12-G10 using Trizol™ reagent (Life Technologies Inc., U.S.A.) following the vendor's instruction. Five micrograms of total RNA were treated with 5 units of Dnase I to remove DNA contaminants and then resuspended in RNase-free water and mixed with 50 ng/μl oligo (dT)$_{12-15}$ primer. The mixture was heated to 70° C. for 10 min and a reaction mixture consisting of 2 μl 10× PCR buffer and and 2 μl 25 mM MgCl$_2$, 1 μl 10 mM dNTPs and 2 μl 0.1M DTT was added following incubation at 42° C. for 5 min. 200 units of Superscript II reverse transcriptase was added and incubated at 42° C. for 50 min. The reaction was terminated at 70° C. for 15 min. To remove the residual RNA, 1 μl of RNase H was added and incubated for 20 min at 37° C. After RNase H digestion, one-tenth of the cDNA products was used to amplify the heavy and light chain genes. PCR reaction was performed using as follows: 1 cycle of 4 min at 95° C., 30 cycles of 30 sec at 95° C., 30 sec at 55° C., 1 min at 72° C., with a final extension step of 7 min at 72° C. The primers used for PCR amplification are as Table 1:

TABLE 1

Primers for PCR

A. Heavy chain

CKVHBACK    5'-GCCGTGACGTTGGACGAGTCC-3'
             A   V  T  L  D  E  S

CKVHFOR
             5'-GGAGGAGACGATGACTTCGGT-3'
              S  S  V  I  V  E  T

B. Light chain

CKVLBACK    5'-GCGCTGACTCAGCCGTCCTCG-3'
             A  L T   Q P  S S

CKVLFOR
             5'-TAGGACGGTCAGGGTTGTCCC-3'
              L   V T  L  T T   G aCKVHBACK, reverse primer for heavy chain variable region.
CKVHFOR, forward primer for heavy chain.
CKVLBACK, reverse primer for light chain variable region.
CKVLFOR, forward primer for light chain. Amino acid sequences encoded by these primers are shown in a single letter code.

Immunoglobulin variable region genes were amplified using the oligonuclcoetides pairs (Table 1): CKVLBACK (λVL reverse primer) and CKVLFOR (λVL forward primer) for the variable region of λ-light chains; CKVHBACK (VH reverse primer) and CKVHBACK(VH forward primer) for the variable region of heavy chains. The PCR products were separated on 1% agarose gel in 1× TAE and extracted using QiaEXII DNA extraction kit (Qiagen, U.S.A.). Purified PCR products were cloned into pGEM-T vector (Promega, U.S.A.) and transformed into JM109 (Promega, U.S.A.) as described (Sambrook, J. et al., *Molecular Cloning*: A Laboratory Mannual. Cold Spring Harbor Laboratory Press. Cold Spring Harbor, N.Y. (1991)).

The process described is shown in FIG. 1.

VI. Sequencing of the Cloned Variable Domain Genes

Plasmid DNA was prepared with a Qiagen plasmid purification kit and sequenced with an ABI 377 automatic sequencer using a big-dye terminator cycles sequencing ready kit (PE Applied Biosystems, U.S.A.). The sequences obtained were analyzed by comparing with germline VH1-JH and V1$_\lambda$-J$_\lambda$ sequences of CB strain (Reynaud, C. A. et al., *Cell*, 48:379-388(1987); and Reynaud, C. A. et al., *Cell*, 59:171-183(1989)).

VII. Preparation of Recombinant scFv Gene

VII-1. Preparation of Recombinant scFv Gene from 2-1 and 5D11 Hybridoma Cell Lines Using cDNA of variable regions obtained from 2-1 and 5D11 hybridoma cell lines, overlap-extension PCR was carried out to amplify genes of recombinant variable regions (Horton, R. M. et al., *Gene*, 77:61-68(1989)). $V_L$-GS linker-$V_H$ (LH construct) and $V_H$-GS linker-$V_L$ gene (HL construct) were amplified through PCR using 100 ng of each of purified $V_L$ and $V_H$ genes, 50 pmole of each of $V_L$ and $V_H$ specific primers (Table 2) and 5 units of Taq DNA polymerase (Promega, Madison, Wis.) by 15 cycles for 1 min at 95° C. and 4 min at 75° C. and final extension for 10 min at 72° C.

The PCR products include intervening GS linker between variable region genes. The GS linker consists of 15 amino acids such as glycine and serine, linking variable regions of heavy and light chains to aid antibody action. The amino acid sequence of GS linker is: N-gggsgggsgggsggs-C.

Figure 6:
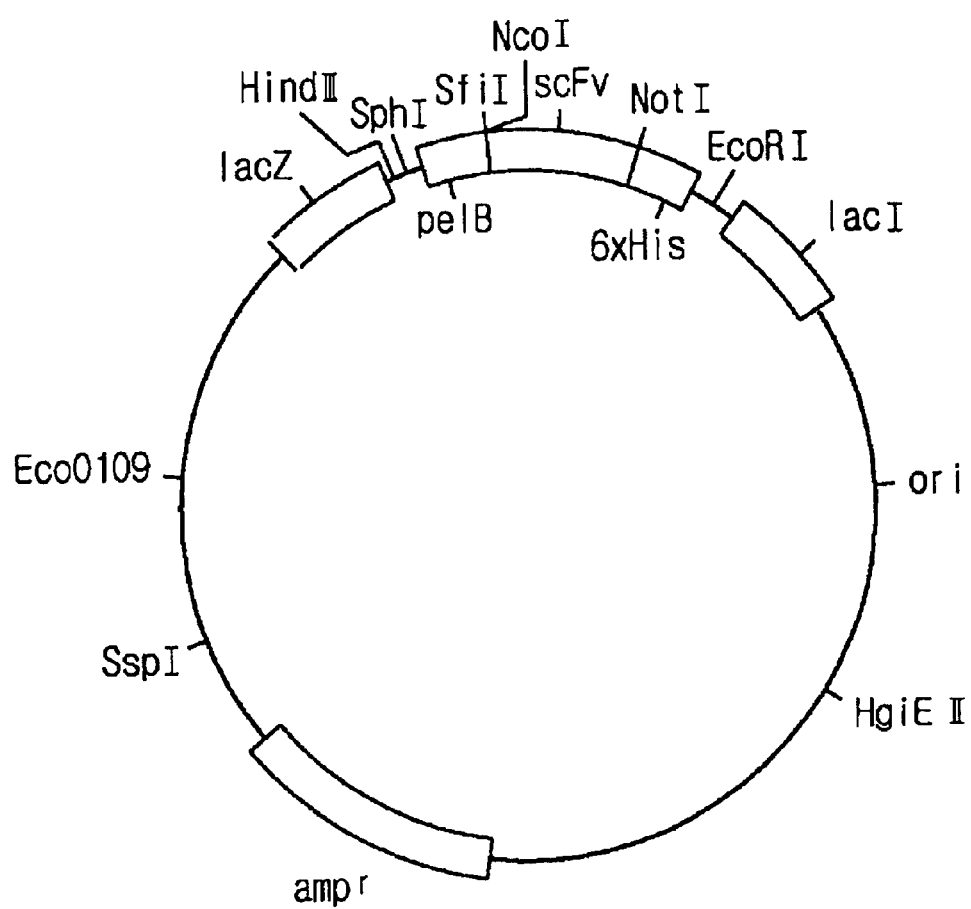
FIG. 6 is a genetic map of the expression vector of one embodiment of this invention.

Thereafter, the PCR products were reamplified using scFv (single chain variable fragment) primers containing Sfi I or Not I restriction enzyme sites (Table 2) by 1 cycle for 4 min at 95° C., 30 cycles for 1 min at 60° C., 1 min at 72° C. and 1 min at 94° C. and final extension for 7 min at 72° C. Reamplified products were digested with Sfi I and Not I (Promega) and cloned into a scFv expression vector derived from pUC119 and containing a 5' Pel B leader sequence and 3' hexahistidine tag (Kim, J. K. et al., *Eur. J. Immunol.*, 24:542-548(1994)). The resulting expression vector has a genetic map of FIG. 6.

TABLE 2

Primers used for PCR amplification of chicken immunoglobulin variable regions and for construction of scFv

| LH construct | HL construct |
|---|---|
| For light chain | |
| $V_LB$, 5'-gcgctgactcagc cgtcctcg-3' | $V_LB$, 5'-ggcggaggtggctctggc ggtggcggatcggcgctgactcagcc gtcctcg-3' |
| $V_LF$, 5'-agagccacctccg cctgaaccgcctccacctagg acggtcaggggttgtccc-3' | $V_LF$, 5'-taggacggtcagggttgt ccc-3' |

TABLE 2-continued

Primers used for PCR amplification of
chicken immunoglobulin variable
regions and for construction of scFv

| LH construct | HL construct |
|---|---|
| For heavy chain | |
| V$_H$B, 5'-ggcggaggtggct ctggcggtggcggatcggccg tgacgttggacgagtcc-3' | V$_H$B, 5'-gccgtgacgttggacgag tcc-3' |
| V$_H$F, 5'-ggaggagacgatg acttcggt-3' | V$_H$F, 5'-agagccacctccgcctga accgcctccaccggaggagacgatga cttcggt-3' |
| For scFv | |
| V$_L$BSfi, 5'-gtcctcgcaa ctg<u>ggcccagccggc</u>catg gccgcgctgactcagccgt cctcg-3' | V$_L$BSfi, 5'-gtcctcgcaactgcg <u>gcccaGcc</u>gggccatggccgccgtga cgttggacgagtcc-3' |
| V$_H$FNot, 5'-ggccacctttg<u>cggc</u> <u>gcggccgc</u>ggaggagacgatg acttcggt-3' | V$_H$FNot, 5'-ggccacctttg<u>cggc</u> cgctaggacggtcagggttgtccc-3' |

V$_L$B, reverse primer for light chain variable region;
V$_L$F, forward primer for light chain variable region;
V$_H$B, reverse primer for heavy chain variable region;
V$_H$F, forward primer for heavy chain variable region.
Underlines show inserted restriction sites for Sfi I or Not I.

VII-2. Preparation of Recombinant scFv Gene from 6D-12-G10 Hybridoma Cell Line

Using CDNA of variable regions obtained from 6D-12-G10 hybridoma cell line, overlap-extension PCR was carried out to amplify genes of recombinant variable regions (Horton, R. M. et al., *Gene*, 77:61-68(1989)). V$_H$-EK linker-V$_L$ gene (HL construct) was amplified from the 100 ng of cDNA by PCR using 50 pmole of the following primer pairs and 5 units of Taq DNA polymerase (Promega). V$_H$ forward primer (V$_H$FSfi, Sfi I restriction site is underlined): 5'-gtcctcgcaactgc<u>ggcccagccggcc</u>atggccgccgtgacgttggacgag tcc-3', V$_H$ reverse primer (V$_H$R): 5'-ttcaccactcccgggtttgcc gctaccggaagtagagccggaggagacgatgacttc-ggtcccgtggcc-3'; V$_L$ forward primer (V$_L$F): 5'-agcggcaaacccgggagtggtgaaggt agcactaaaggtgcgctgactcagccgtc-ctcggtgtcagca-3'; V$_L$ reverse primer (V$_L$RNot, Not I restriction site is underlined): 5'-ggccacctttg<u>cggccgc</u>taggacggtcagggttgtccc-3'. PCR was performed for 1 cycle for 4 min at 95° C., 30 cycles for 30 sec at 55° C., 1 min at 72° C. and 30 sec at 95° C. and final extension for 7 min at 72° C. PCR products were resolved on 1.5% agarose gels and recovered using the QIAEX II gel extraction kit (Qiagen, Valencia, Calif.).

The PCR products include intervening EK linker between variable region genes. The EK linker consists of 18 amino acids such as glutamic acid and lysine, linking variable regions of heavy and light chains to aid antibody action. The amino acid sequence of EK linker is: N-gstsgsgkpgsgegstkg-C.

Purified V$_H$ and V$_L$ genes (100 ng each) were mixed and reamplified with Taq DNA polymerase (Promega) and primers V$_H$FSfi and V$_L$RNot for 15 cycles for 1 min at 95° C. and 4 min at 75° C. with final extension for 10 min at 72° C. to produce the assembled scFv gene. The reamplified product was digested with Sfi I and Not I (Promega) and cloned into corresponding sites of a scFv expression vector derived from pUC119 and containing a 5' Pel B leader sequence and 3' hexahistidine tag (Kim, J. K. et al., *Eur. J. Immunol.*, 24:542-548(1994)). The resulting expression vector has a genetic map of FIG. 6.

VIII. Expression and Purification of scFv Antibodies

Vectors containing scFv genes were transformed into competent *E. coli* BMH71-18 (obtained from Dr. E. Sally Ward, Southern Western Medical Center, University of Texas, U.S.A.) according to Hanahan method (Kim, J. K. et al., *Eur. J. Immunol.*, 24:542-548(1994)). Transformed bacteria were grown at 30° C. overnight with constant agitation in 2× TY broth (20 g tryptone, 10 g yeast extract, 10 g NaCl/liter) (Difco, Detroit, Mich.) containing 100 μg/ml ampicillin (Sigma, St. Louis, Mo.) and 1% (w/v) glucose, harvested by centrifugation at 3,500 rpm for 10 min at room temperature and washed once with 2× TY broth. The bacteria were resuspended in 2× TY broth containing 100 μg/ml ampicillin and 1.0 mM isopropyl—D-thiogalactopyranoside (Gold Biotechnology, St. Louis, Mo.) and induced for 5-6 h at 25° C. with shaking at 180 rpm.

To purify recombinant scFv antibodies, bacteria were harvested by centrifugation at 4° C., sonicated on ice in 250 mM NaCl, 50 mM Tris-HCl, pH 7.5 and 1.0 mg of lysozyme (Sigma), cell debris removed by centrifugation at 10,000 rpm for 30 min at 4° C., the supernatants applied to Ni-NTA His-bind resin column (Novagen, Madison, Wis.) and bound antibodies recovered according to the manufacturers instructions.

Purified antibodies were resuspended in sodium dodecyl sulfate-polyacrylamide gel electrophoresis (SDS-PAGE) sample buffer (0.125 M Tris-HCl, pH 6.8, 4% SDS, 20% glycerol, 10% 2-mercaptoethanol, 0.004% bromophenol blue), heated at 94° C. for 4 min, separated on 15% SDS-polyacrylamide gels using a Mini-Protean II electrophoresis apparatus (Bio-Rad, Hercules, Calif.) and stained with 0.25% Coomassie blue in 10% acetic acid/50% methanol.

IX. ELISA (Enzyme-Linked Immunosorbent Assay)

Flat bottom 96-well microtiter plates (Costar, Boston, Mass.) were coated with 100 μl of Eimeria antigen (10 mg/ml) in 0.1 M sodium carbonate buffer, pH 9.6 at 4° C. overnight and washed 3 times with PBS, pH 7.2 containing 0.05% Tween-20 (PBS-T). Wells were blocked with 200 μl of PBS containing 1% bovine serum albumin (BSA; Sigma) for 1 h at room temperature, washed 3 times with PBS-T, 100 μl of recombinant antibody (100 μg/ml) in PBS-1% BSA added and incubated for 2 h at room temperature. Following washing 3 times with PBS-T, 100 μl/well of horseradish peroxidase-conjugated polyhistidine monoclonal antibody (Sigma) diluted 1:3,000 in PBS-1% BSA was added, incubated for 40 min at room temperature and washed 4 times. Peroxidase activity was detected with 100 μl of 0.01% (w/v) tetramethylbenzidine (Sigma) in 0.05 M phosphate-citrate buffer, pH 5.0 for 10 min, the reaction was stopped with 50 μl of 2 N H$_2$SO$_4$ and the optical density at 450 nm measured on a microtiter plate reader (Bio-Rad).

X. IFA (Immunofluorescence Assay)

Air-dried sporozoites on pre-cleaned glass slides (Corning, Corning, N.Y.) were incubated with 100 μl of recombinant scFv antibody for 40 min at room temperature and washed 3 times with PBS. Slides were incubated for 40 min at room temperature with 100 μl of polyhistidine antibody diluted 1:3,000 in PBS-1% BSA, washed 4 times, incubated for 40 min with 100 μl of fluorescein isothiocyanate (FITC)-labeled rabbit anti-mouse IgG (1:3,000 in PBS-1% BSA) and washed 3 times. Slides were counterstained with 0.01% Evans blue, washed 3 times, mounted in Vectashield Mounting medium (Vector, Burlingame, Calif.) and photographed with an epifluorescence microscope equipped with a 40× objective and a Texas Red/FITC dual wavelength filter set (Carl Zeiss, Germany).

XI. Immunoblot Analysis

Eimeria antigens were resuspended in SDS-PAGE sample buffer, heated and resolved on 15% SDS-polyacrylamide gels as described above. Separated proteins were electrophoretically transferred to Immobilon-P membrane (Millipore, Bedford, Mass.) using the Mini-Protean II transfer chamber (Bio-Rad), the membrane blocked overnight at 4° C. in PBS containing 1% nonfat dry milk, washed 2 times with PBS-T and sequentially incubated at room temperature with recombinant scFv antibody (1:1,600 in PBS-1% BSA) for 40 min and horseradish peroxidase-conjugated polyhistidine antibody (1:3,000 in PBS-1% BSA) for 40 min. The membrane was washed 5 times with PBS-T, 5 times with distilled water and developed using Sigma Fast DAB peroxidase substrate (Sigma).

RESULTS

Figure 2:
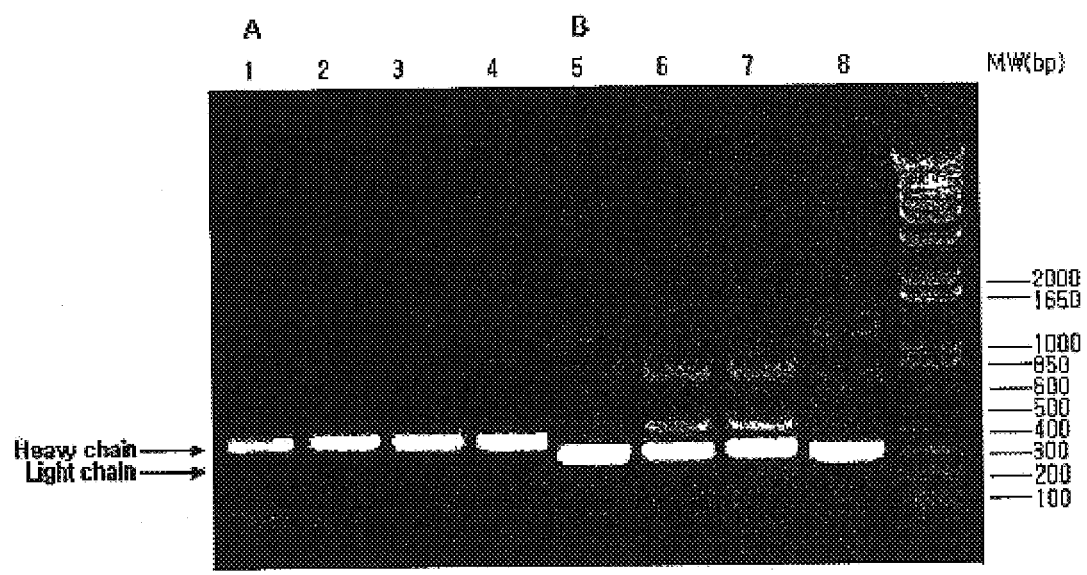
FIG. 2 is a photograph showing amplified PCR products of DNA molecules encoding heavy and light chain variable regions derived from hybridomas.

I. PCR Amplification of Variable Regions of Heavy and λ-Light Chains of Chicken Monoclonal Antibodies The PCR products were subjected to electrophoresis on agarose gel to confirm their correct size (see FIG. 2). In FIG. 2, A represents heavy chains, lane 1 5D11, lane 2 8C3, lane 3 13C8, and lane 4 2-1 hybridoma cells; and B represents λ-light chain, lane 5 5D11, lane 6 8C3, lane 7 13C8, and lane 8 2-1 hybridoma cells. As shown in FIG. 2, the size of DNAs encoding heavy and λ-light chain is about 340 bp and 325 bp, respectively. As known in methods aforementioned, the possibility of PCR products templated from genomic DNA was excluded because Dnase I digestion was performed before cDNA synthesis to remove genomic DNA.

II. Sequence Analysis of Cloned Variable Regions of Chicken Heavy and λ-Light Chains Nucleotide sequences of the cloned variable regions of heavy chain obtained from five hybridoma cells including 2-1, 5D11, 13C8, 8C3 and 6D-12-G10 are represented in SEQ ID NOs: 17, 19, 21, 23 and 38, respectively. Nucleotide sequences of variable regions of λ-light chains from each of hybridoma cells are represented in SEQ ID NOs: 25, 27, 29, 31 and 40, respectively.

FIGS. 3a, 3b, 3c and 3d represent the sequence comparison between the above nucleotide sequences and germline VH1-JH and V1$_\lambda$-J$_\lambda$ sequences of CB strain. In FIGS. 3a and 3b, the nucleotide identities are indicated by dots and the absence of corresponding residues is shown by dashes. In FIGS. 3c and 3d, the nucleotide identities are indicated by asterisk and the absence of corresponding residues is indicated by a colon.

In figures, the regions of complementary determining region (CDR) and PCR primers are indicated with underlines in the germline sequences. Base substitution and addition are shown in bold and italic, respectively, in λ-light chains. Framework (FR) and CDR are determined according to the method described in Kabat, E. A. et al., *Sequences of proteins of immunological interest*. U.S. Depat. Health and Human Services, NIH publication No. 91-3242, 5$^{th}$ ed. (1991).

Through the sequence comparison study, the difference of sequences is mainly found in CDRs. For example, the insertion of 15 nucleotides (gctggaagttactat) was observed in the CDR1 in the λ-light chain of 2-1 clone. The CDR3 of the 13C8 clone and 8C3 clone also contain the insertion of 15 nucleotides (gatagtgattatgtt) and 6 nucleotides (atttat), respectively. The deletions were found in 4 different clones. For example, 3 nucleotides (gca) in the CDR3 were deleted in 2-1 clone and in the case of 13C8 and 8C3 clones, 3 different nucleotides (agc) in CDR3 were deleted. 3 nucleotides deletion was observed in CDR3 of the V$_L$ cDNA of 6D-12-G10.

Gene conversion was traced by comparing the variable region of λ-light chain nucleotide sequences with 25 pseudogenes of the CB strain (Reyanud, C. A., et al., *Cell*, 48:379-388(1987)) and other known pseudogenes in different chicken strains (Kondo, T. H. et al., *Eur. J. Immunol.*, 23:245-249(1993)), of which results are demonstrated in FIG. 5. For example, both the CDR1 and CDR2 of the 2-1 clone was derived from ΨVλ8. These CDRs were derived from ΨVλ14 and ΨVλ7 in the 5D11 clone, ΨV23 and ΨV12 in the 8C3 clone, and ΨV14 and, ΨV14 and ΨV12 or ΨV13 in the 13C8 clone. It was observed that VL cDNA of 6D-12-G10 shared a 196 bp region (nucleotides 49-244) identical with pseudogene Ψ7.

The gene conversion found in this invention showed characteristics similar to those reported previously for the number of gene conversion events in rearranged variable genes(Lillehoj, H. S. et al., *Avian Dis.*, 44:408-425(2000)). The boundary of the donor pseudogene and germline gene was not clear, and sometimes more than one candidate pseudogene was found, indicating the multiple gene conversion events in one variable region.

These data clearly suggest that most of the distinct differences between the cloned genes and the most closely matching known germline sequences of the λ-light chain can be accounted for by conversions with the pseudo-VL gene sequences (Reyanud, C. A., et al., *Cell*, 48:379-388(1987)). In addition, as known in FIG. 3, sixteen single nucleotide substitutions were found after identification of donor pseudogenes, suggesting a possible somatic hypermutation. Among 16 mutations found in the Vλ1 genes, 8 mutations were located in the CDRs and 8 mutations were located in the FR in all clones. Since clusters (7 out of 8) of point mutations in CDR are found in CDR3, the base substitutions in CDR3 are likely to be somatic hypermutations.

Since the results shown above are those of mature immunoglobulin molecules from chicken hybridoma, it was assumed that more mutations could be accumulated in CDRs as a result of affinity selection of B cells. The sequence analysis was not made with the heavy chains as the complete set of pseudo-VH sequences and germline D region sequences were not determined (Reynaud, C. A. et al., *Cell*, 59:171-183(1989); and Rose, M. E. et al., *Immune response in parasitic Infections; Immunology, Immunopathology, Immunoprophylaxis*, CRC Press, Boca Raton, Fla., p.275 (19$^{87}$)). However, as shown in FIGS. 3 and 4, the sequence differences were mainly found between the five clones and germline, specially in the CDRs of heavy chains.

Although germline and pseudogene sequences of the White Leghorn strain have not yet been analyzed, it is suggested that the primers used in this study can be effective for obtaining chicken variable region genes by PCR. In fact, for most White Leghorn lines, DNA polymorphism is negligible in the 5' and 3' ends of the variable region in both heavy and λ-light chains (Benatar, T. et al., *Eur. J. Immunol.*, 23:2448(1993)). FIGS. 4a and 4b represent the sequence comparison between the above nucleotide sequences and germline VH1-JH and V1$_\lambda$-J$_\lambda$ sequences of CB strain. In FIGS. 4a and 4b, amino acid identity is shown by dots, the absence of corresponding residues is shown by dashes and amino acid residues derived from D gene in the heavy chain are shown by an X.

Amino acid sequence differences between the cloned genes and germline of the CB strain shown in FIGS. 4a and 4b are consistent with FIGS. 3a and 3b indicating that differences between the cloned genes and germline were predominantly in the CDRs in both heavy and λ-light chains.

As shown FIGS. 4a and 4b, the amino acid sequences of the CDRs of 5 different clones are very different. It suggest that the antibodies derived from 5 different clones may recognize the different epitopes of Bimeria surface antigens since antigen binding specificity is based on the encoded combining site specificity mostly dominated by the CDR regions in the heavy and light chains.

In conclusion, all the sequences elucidated in this invention show enough evidence of extensive and varied gene conversion of the single rearranged variable gene in both heavy and λ-light chains. Moreover, the gene conversion contributing to immunoglobulin gene diversification in chickens can simplify the production of the chicken recombinant antibody fragments using a single pair of primers as used in this invention.

III. Cloning and Expression of scFv Genes

Figure 9A:
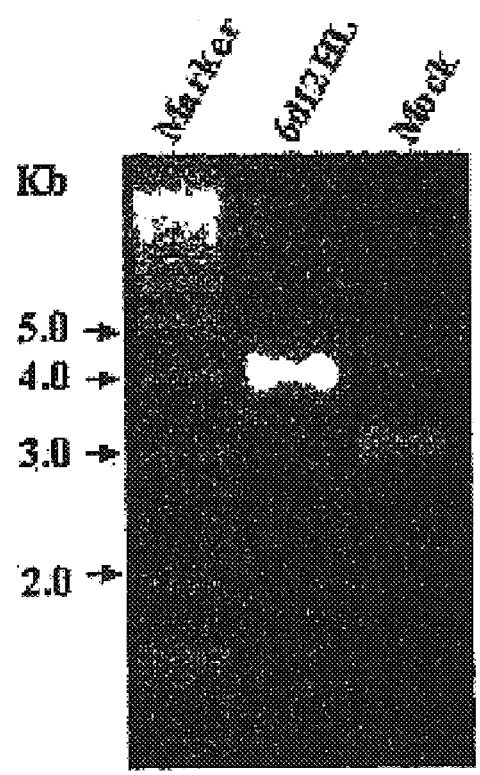
FIG. 9a is a photograph demonstrating incorporation of nucleotide sequence encoding scFv antibody derived from 6D-12-G10 hybridoma into expression vector.

The sizes of the scFv recombinants derived from 2-1, 5D11, 13C8 and 8C3 were confirmed by Not I enzyme digestion and gel electrophoresis. All showed about 4.0 kb band corresponding to the intact recombinant plasmid before restriction enzyme digestion and about 720-730 bp insert after digestion. In addition, the non-recombinant and recombinant plasmids carrying scFv genes derived from 6D-12-G10 were digested with Not I and analyzed on agarose gel (see FIG. 9a). The size difference between the two observed bands (approximately 750 bp) corresponds to the expected size of the scFv insert based on its nucleotide sequence.

From the culture of transformed E. coli host, 5-10 mg/liter of purified scFv were typically obtained. This result indicates that soluble, stable and functional scFv chicken antibodies of this invention can be produced with higher yield on a consistent basis, using preferable expression host such as E. coli. In contrast, it was found that chicken hybridoma cells generally produce low quantities of antibodies (about 10% of that produced by murine hybridomas), easily segregate and lose their ability to produce antibodies and are incapable of forming ascites fluids. The drawbacks of the conventional methods using hybridoma cells can be overcome according to the present invention. Using recombinant antibodies of this invention, the anti-coccidia antibody can be obtained 50-70 times, in shorter period, as much as the conventional methods using hybridoma cells (about 0.1 mg/liter of culture).

Figure 7:
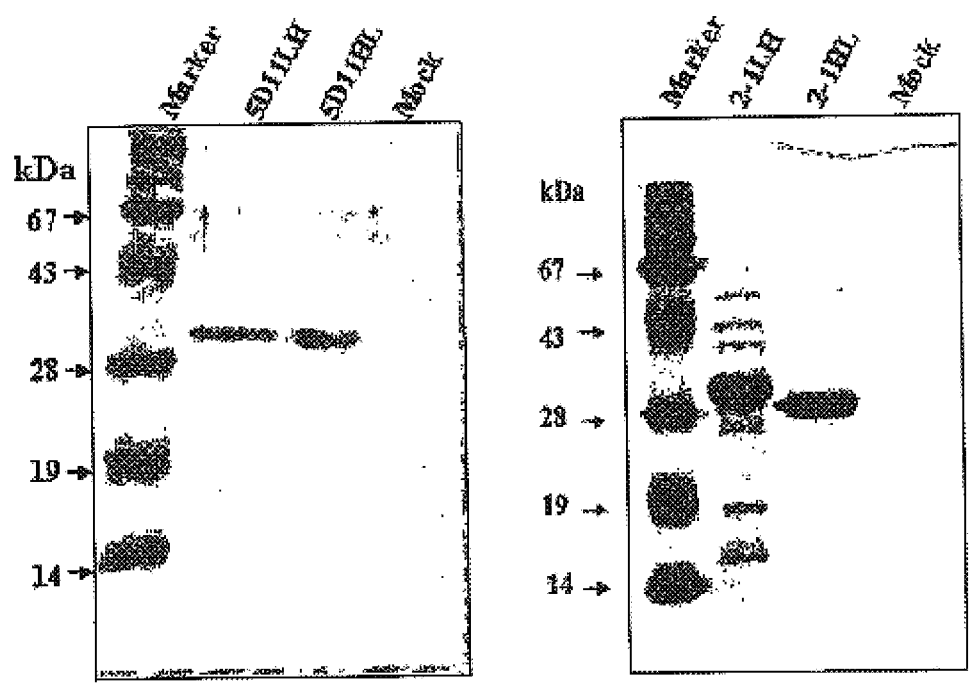
FIG. 7 is a photograph showing SDS-PAGE analysis of scFv antibodies of this invention.
Figure 9B:
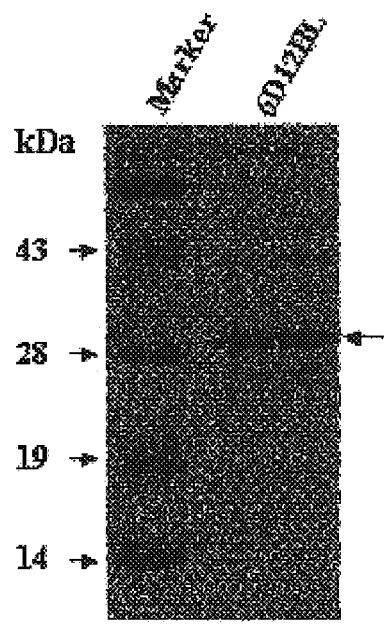
FIG. 9b is a photograph showing SDS-PAGE analysis of scFv antibody of this invention, 6D12HL.

As shown in FIG. 7, SDS-PAGE analysis of purified recombinant antibodies, 5D11LH, 5D11HL and 2-1LH revealed homogeneous proteins with apparent molecular weights of approximately 31 kDa while the 2-1HL antibody was about 30 kDa. In addition, as demonstrated in FIG. 9b, purified recombinant antibody 6D12HL exhibited about 31.0 kDa of molecular weight.

IV. Antigen Binding Characteristics of scFv Antibodies

ELISA, IFA and immunoblot assay elucidated antigen binding characteristics of scFv antibodies including 5D11LH, 5D11HL, 2-1LH and 2-1HL.

Figure 8:
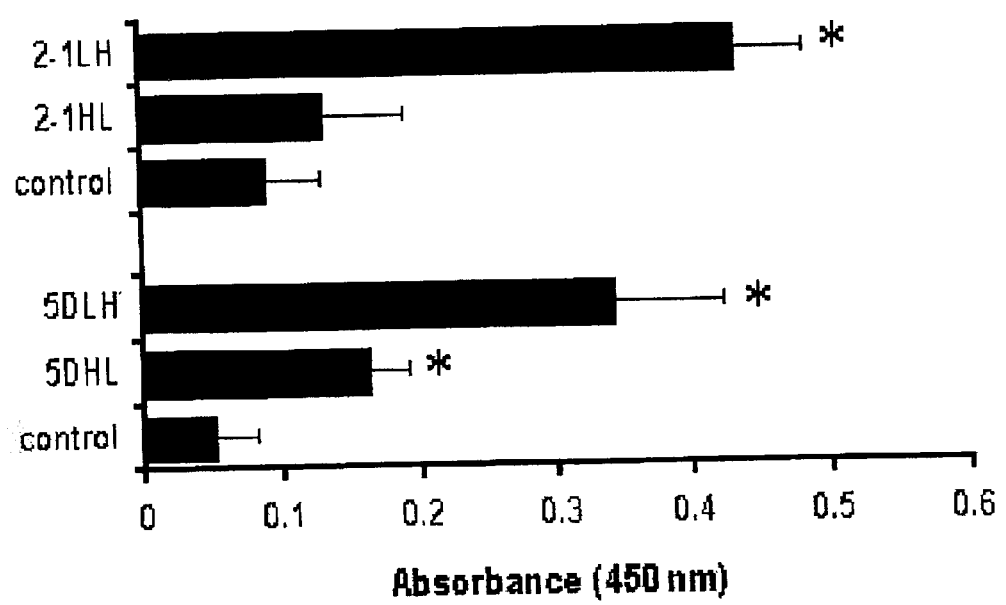
FIG. 8 shows ELISA analysis demonstrating antigen-binding capacity of scFv of this invention.

As shown in FIG. 8, antibodies 2-1LH, 5D11LH and 5D11HL showed greater binding activity to ELISA microwells coated with E. aeruvulina sporozoite antigens compared with the BSA negative control. Antibody 2-1HL was non-reactive with Eimeria antigens. Similarly, by whole parasite IFA, the 2-1LH, 5D11LH and 5D11HL antibodies were reactive with E. acervulina surface antigens.

Although scFv antibodies are frequently constructed as $V_H$-linker-$V_L$ chain (H-L) sequences(de Haard H, Henderikx P., et al., Adv. Drug Deliv. Rev., 31:5-31(1998)), the present inventors observed better antigen binding with the 5D11LH and 2-1LH antibodies compared with the corresponding H-L antibodies. In fact, the 2-1HL antibody was nonreactive with Eimeria antigens by any of the methods used. In this respect, it is noteworthy that a few previously described murine H-L chain combinations did not generate functional antibodies due to the requirement for N- and/or C-terminal regions of the $V_H$ and $V_L$ chains for antigen binding (de Haard H, Henderikx P., et al., Adv. Drug Deliv. Rev., 31:5-31(1998); and Padlan, E. A., Mol. Immunol., 28:489-498(1991)).

Figure 10:
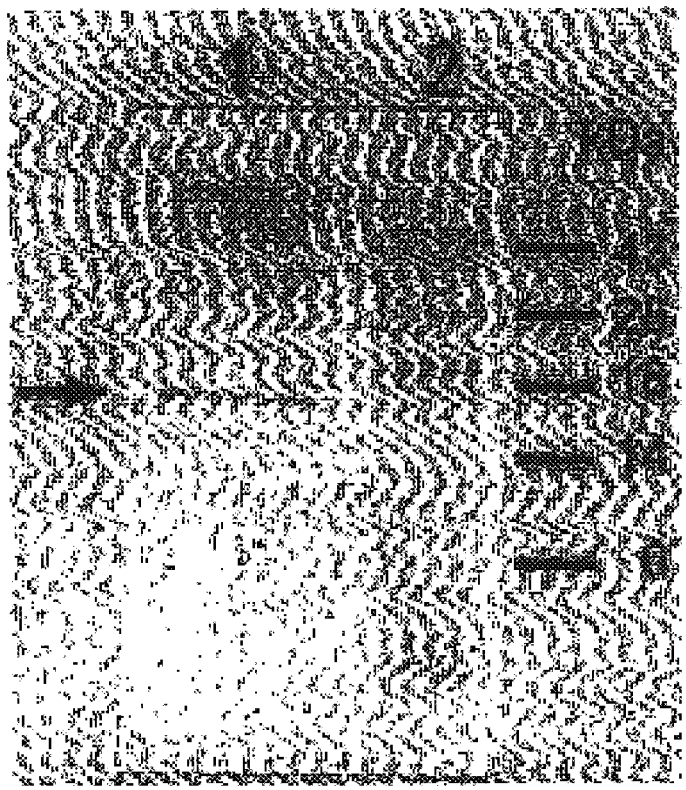
FIG. 10 is a photograph representing immunoblotting analysis of scFv antibody of this invention, 6D12HL.
Figure 11:
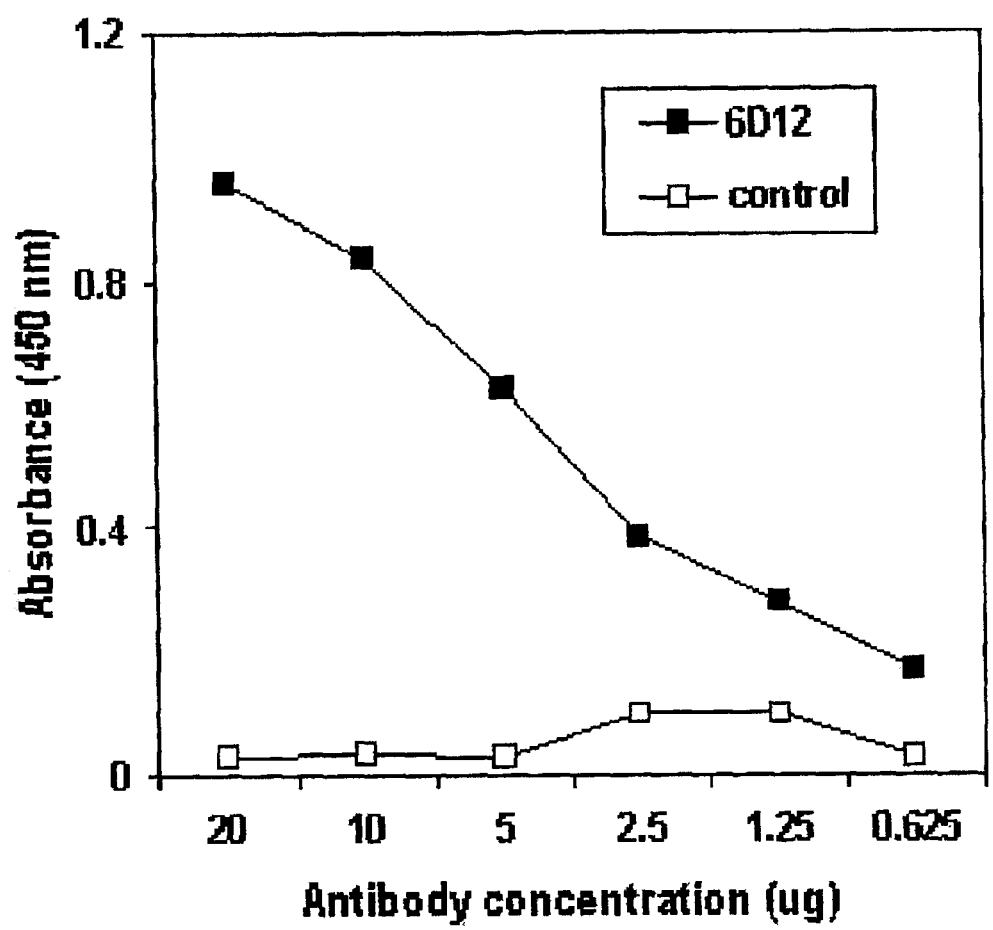
FIG. 11 shows ELISA analysis demonstrating antigen-binding capacity of scFv of this invention, 6D12HL.

In FIG. 10 showing the result of immunoblot assay of 6D12HL, E. acervulina proteins of 17 kDa are detected by 6D12HL antibodies. In FIG. 10, lanes 1 and 2 represent 6D12HL and molecular marker, respectively. FIG. 11 showing the ELISA result of 6D12HL demonstrates that 6D12HL antibody has dose-dependent reactivity with soluble E. acervulina sporozoite antigens. According to IFA, 6D12HL antibody is reactive with the apical region of E. acervulina sporozoites.

As described above, recombinant scFv antibodies of this invention show about 31 kDa in size, which are approximately one fifth the size of an intact IgG molecule, and exhibit a binding capacity to specific antigen. Consequently, the recombinant scFv antibodies of this invention have superior tissue penetration properties, an important consideration given the invasive nature of Eimeria parasites. Furthermore, the ability to purify relatively large quantities of functional scFv antibodies enables passive immunity to coccidiosis as well as provides valuable reagents for affinity purification of potential Eimeria vaccine antigens.

Having described a preferred embodiment of the present invention, it is to be understood that variants and modifications thereof falling within the spirit of the invention may become apparent to those skilled in this art, and the scope of this invention is to be determined by appended claims and their equivalents.

SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: forward primer for PCR amplification of heavy
    chain variable region -continued

```
<400> SEQUENCE: 1
ggaggagacg atgacttcgg t                                              21

<210> SEQ ID NO 2
<211> LENGTH: 21
<212> TYPE: DNA
<213> ORGANISM: Artificial Sequence
<220> FEATURE:
<223> OTHER INFORMATION: reverse primer for PCR amplification of heavy
      chain variable region

<400> SEQUENCE: 2
gccgtgacgt tggacgagtc c                                              21

<210> SEQ ID NO 3
<211> LENGTH: 21
<212> TYPE: DNA
<213> ORGANISM: Artificial Sequence
<220> FEATURE:
<223> OTHER INFORMATION: forward primer for PCR amplification of light
      chain variable region

<400> SEQUENCE: 3
taggacggtc agggttgtcc c                                              21

<210> SEQ ID NO 4
<211> LENGTH: 21
<212> TYPE: DNA
<213> ORGANISM: Artificial Sequence
<220> FEATURE:
<223> OTHER INFORMATION: reverse primer for PCR amplification of light
      chain variable region

<400> SEQUENCE: 4
gcgctgactc agccgtcctc g                                              21

<210> SEQ ID NO 5
<211> LENGTH: 51
<212> TYPE: DNA
<213> ORGANISM: Artificial Sequence
<220> FEATURE:
<223> OTHER INFORMATION: reverse primer for PCR amplification of heavy
      chain variable region

<400> SEQUENCE: 5
ggcggaggtg gctctggcgg tggcggatcg gccgtgacgt tggacgagtc c             51

<210> SEQ ID NO 6
<211> LENGTH: 21
<212> TYPE: DNA
<213> ORGANISM: Artificial Sequence
<220> FEATURE:
<223> OTHER INFORMATION: reverse primer for PCR amplification of heavy
      chain variable region

<400> SEQUENCE: 6
ggaggagacg atgacttcgg t                                              21

<210> SEQ ID NO 7
<211> LENGTH: 21
<212> TYPE: DNA
<213> ORGANISM: Artificial Sequence
<220> FEATURE:
<223> OTHER INFORMATION: reverse primer for PCR amplification of light
      chain variable region
```

```
<400> SEQUENCE: 7
gcgctgactc agccgtcctc g                                              21

<210> SEQ ID NO 8
<211> LENGTH: 51
<212> TYPE: DNA
<213> ORGANISM: Artificial Sequence
<220> FEATURE:
<223> OTHER INFORMATION: forward primer for PCR amplification of light
      chain variable region

<400> SEQUENCE: 8
agagccacct ccgcctgaac cgcctccacc taggacggtc agggttgtcc c             51

<210> SEQ ID NO 9
<211> LENGTH: 21
<212> TYPE: DNA
<213> ORGANISM: Artificial Sequence
<220> FEATURE:
<223> OTHER INFORMATION: reverse primer for PCR amplification of heavy
      chain variable region

<400> SEQUENCE: 9
gccgtgacgt tggacgagtc c                                              21

<210> SEQ ID NO 10
<211> LENGTH: 51
<212> TYPE: DNA
<213> ORGANISM: Artificial Sequence
<220> FEATURE:
<223> OTHER INFORMATION: forward primer for PCR amplification of heavy
      chain variable region

<400> SEQUENCE: 10
agagccacct ccgcctgaac cgcctccacc ggaggagacg atgacttcgg t             51

<210> SEQ ID NO 11
<211> LENGTH: 51
<212> TYPE: DNA
<213> ORGANISM: Artificial Sequence
<220> FEATURE:
<223> OTHER INFORMATION: reverse primer for PCR amplification of light
      chain variable region

<400> SEQUENCE: 11
ggcggaggtg gctctggcgg tggcggatcg gcgctgactc agccgtcctc g             51

<210> SEQ ID NO 12
<211> LENGTH: 21
<212> TYPE: DNA
<213> ORGANISM: Artificial Sequence
<220> FEATURE:
<223> OTHER INFORMATION: forward primer for PCR amplification of light
      chain variable region

<400> SEQUENCE: 12
taggacggtc agggttgtcc c                                              21

<210> SEQ ID NO 13
<211> LENGTH: 55
<212> TYPE: DNA
<213> ORGANISM: Artificial Sequence
<220> FEATURE:
<223> OTHER INFORMATION: reverse primer for PCR amplification of scFv

<400> SEQUENCE: 13
```

```
gtcctcgcaa ctgcggccca gccgggccat ggccgcgctg actcagccgt cctcg        55

<210> SEQ ID NO 14
<211> LENGTH: 39
<212> TYPE: DNA
<213> ORGANISM: Artificial Sequence
<220> FEATURE:
<223> OTHER INFORMATION: forward primer for PCR amplification of scFv

<400> SEQUENCE: 14
ggccaccttt gcggccgcgg aggagacgat gacttcggt                          39

<210> SEQ ID NO 15
<211> LENGTH: 55
<212> TYPE: DNA
<213> ORGANISM: Artificial Sequence
<220> FEATURE:
<223> OTHER INFORMATION: reverse primer for PCR amplification of scFv

<400> SEQUENCE: 15
gtcctcgcaa ctgcggccca gccgggccat ggccgccgtg acgttggacg agtcc        55

<210> SEQ ID NO 16
<211> LENGTH: 39
<212> TYPE: DNA
<213> ORGANISM: Artificial Sequence
<220> FEATURE:
<223> OTHER INFORMATION: forward primer for PCR amplification of scFv

<400> SEQUENCE: 16
ggccaccttt gcggccgcta ggacggtcag ggttgtccc                          39

<210> SEQ ID NO 17
<211> LENGTH: 369
<212> TYPE: DNA
<213> ORGANISM: chicken hybridoma cell line 2-1
<220> FEATURE:
<221> NAME/KEY: CDS
<222> LOCATION: (1)..(369)

<400> SEQUENCE: 17 gcc gtg acg ttg gac gag tcc ggg ggc ggc ctc cag acg ccc gga gga    48
Ala Val Thr Leu Asp Glu Ser Gly Gly Gly Leu Gln Thr Pro Gly Gly
 1               5                  10                  15 gcg ctc agc ctc gtc tgc aag gcc tcc ggg ttc acc ttc agc agc cat    96
Ala Leu Ser Leu Val Cys Lys Ala Ser Gly Phe Thr Phe Ser Ser His
             20                  25                  30 ggc atg atg tgg gtg cga cag acg ccc ggc aag ggg ctg gag tgg gtc   144
Gly Met Met Trp Val Arg Gln Thr Pro Gly Lys Gly Leu Glu Trp Val
         35                  40                  45 gcg ggt att agc aac act ggt act tac acg tac tac gcg ccg gcg gtg   192
Ala Gly Ile Ser Asn Thr Gly Thr Tyr Thr Tyr Tyr Ala Pro Ala Val
     50                  55                  60 aag ggc cgt gcc acc atc tcg agg gac aac ggg cag agc aca gtg agg   240
Lys Gly Arg Ala Thr Ile Ser Arg Asp Asn Gly Gln Ser Thr Val Arg
 65                  70                  75                  80 ctg cag ctg aac aac ctc agg gct gag gac acc ggc acc tac tac tgc   288
Leu Gln Leu Asn Asn Leu Arg Ala Glu Asp Thr Gly Thr Tyr Tyr Cys
                 85                  90                  95 gcc aaa ggt ggt gct tat tgt gct ggt tgt ggt ggt gac atc gac gca   336
Ala Lys Gly Gly Ala Tyr Cys Ala Gly Cys Gly Gly Asp Ile Asp Ala
            100                 105                 110 tgg ggc cac ggg acc gaa gtc atc gtc tcc tcc                        369
Trp Gly His Gly Thr Glu Val Ile Val Ser Ser
```

<210> SEQ ID NO 18
<211> LENGTH: 123
<212> TYPE: PRT
<213> ORGANISM: chicken hybridoma cell line 2-1

<400> SEQUENCE: 18

```
Ala Val Thr Leu Asp Glu Ser Gly Gly Gly Leu Gln Thr Pro Gly Gly
  1               5                  10                  15
Ala Leu Ser Leu Val Cys Lys Ala Ser Gly Phe Thr Phe Ser Ser His
                 20                  25                  30
Gly Met Met Trp Val Arg Gln Thr Pro Gly Lys Gly Leu Glu Trp Val
             35                  40                  45
Ala Gly Ile Ser Asn Thr Gly Thr Tyr Thr Tyr Tyr Ala Pro Ala Val
         50                  55                  60
Lys Gly Arg Ala Thr Ile Ser Arg Asp Asn Gly Gln Ser Thr Val Arg
 65                  70                  75                  80
Leu Gln Leu Asn Asn Leu Arg Ala Glu Asp Thr Gly Thr Tyr Tyr Cys
                 85                  90                  95
Ala Lys Gly Gly Ala Tyr Cys Ala Gly Cys Gly Gly Asp Ile Asp Ala
                100                 105                 110
Trp Gly His Gly Thr Glu Val Ile Val Ser Ser
            115                 120
```

<210> SEQ ID NO 19
<211> LENGTH: 372
<212> TYPE: DNA
<213> ORGANISM: chicken hybridoma cell line 5D11
<220> FEATURE:
<221> NAME/KEY: CDS
<222> LOCATION: (1)..(372)

<400> SEQUENCE: 19

```
gcc gtg acg ttg gac gag tcc ggg ggc ggc ctc cag acg ccc gga gga    48
Ala Val Thr Leu Asp Glu Ser Gly Gly Gly Leu Gln Thr Pro Gly Gly
  1               5                  10                  15 gcg ctc agc ctc gtc tgc aag gcc tcc ggg ttc gac ttc agc agt tac    96
Ala Leu Ser Leu Val Cys Lys Ala Ser Gly Phe Asp Phe Ser Ser Tyr
                 20                  25                  30 gac atg att tgg gtg cga cag gcg ccc ggc aag ggg ctg gaa tac gtc   144
Asp Met Ile Trp Val Arg Gln Ala Pro Gly Lys Gly Leu Glu Tyr Val
             35                  40                  45 gcg ggt att aga agt gat ggt agt agc ata tac tac ggg gcg gcg gtg   192
Ala Gly Ile Arg Ser Asp Gly Ser Ser Ile Tyr Tyr Gly Ala Ala Val
         50                  55                  60 aag ggc cgt gcc acc atc tcg agg gac aac ggg cag agc act ctg agg   240
Lys Gly Arg Ala Thr Ile Ser Arg Asp Asn Gly Gln Ser Thr Leu Arg
 65                  70                  75                  80 ctg cag ctg aac aac ctc agg gct gag gac acc ggc acc tat tac tgc   288
Leu Gln Leu Asn Asn Leu Arg Ala Glu Asp Thr Gly Thr Tyr Tyr Cys
                 85                  90                  95 gcc aaa agt tct tat ggt agt tgg aga ggt tct act ggt gac atc gac   336
Ala Lys Ser Ser Tyr Gly Ser Trp Arg Gly Ser Thr Gly Asp Ile Asp
                100                 105                 110 gca tgg ggc cac ggg acc gaa gtc atc gtc tcc tcc                   372
Ala Trp Gly His Gly Thr Glu Val Ile Val Ser Ser
            115                 120
```

<210> SEQ ID NO 20

```
<211> LENGTH: 124
<212> TYPE: PRT
<213> ORGANISM: chicken hybridoma cell line 5D11

<400> SEQUENCE: 20

Ala Val Thr Leu Asp Glu Ser Gly Gly Leu Gln Thr Pro Gly Gly
 1               5                  10                  15

Ala Leu Ser Leu Val Cys Lys Ala Ser Gly Phe Asp Phe Ser Ser Tyr
                20                  25                  30

Asp Met Ile Trp Val Arg Gln Ala Pro Gly Lys Gly Leu Glu Tyr Val
            35                  40                  45

Ala Gly Ile Arg Ser Asp Gly Ser Ser Ile Tyr Tyr Gly Ala Ala Val
        50                  55                  60

Lys Gly Arg Ala Thr Ile Ser Arg Asp Asn Gly Gln Ser Thr Leu Arg
 65                  70                  75                  80

Leu Gln Leu Asn Asn Leu Arg Ala Glu Asp Thr Gly Thr Tyr Tyr Cys
                85                  90                  95

Ala Lys Ser Ser Tyr Gly Ser Trp Arg Gly Ser Thr Gly Asp Ile Asp
            100                 105                 110

Ala Trp Gly His Gly Thr Glu Val Ile Val Ser Ser
        115                 120

<210> SEQ ID NO 21
<211> LENGTH: 372
<212> TYPE: DNA
<213> ORGANISM: chicken hybridoma cell line 13C8
<220> FEATURE:
<221> NAME/KEY: CDS
<222> LOCATION: (1)..(372)

<400> SEQUENCE: 21 gcc gtg acg ttg gac gag tcc ggg ggc ggc ctc cag acg ccc gga gga      48
Ala Val Thr Leu Asp Glu Ser Gly Gly Gly Leu Gln Thr Pro Gly Gly
 1               5                  10                  15 ggg ctc agc ctc gtc tgc aag ggc tcc ggg ctc gac ttc agc agt tat      96
Gly Leu Ser Leu Val Cys Lys Gly Ser Gly Leu Asp Phe Ser Ser Tyr
                20                  25                  30 gcc atg ggt tgg gtg cga cag gca ccc ggc aag ggg ctg gaa ttc gtc     144
Ala Met Gly Trp Val Arg Gln Ala Pro Gly Lys Gly Leu Glu Phe Val
            35                  40                  45 gcg ggt att aaa aaa aat gat ggt agt tgg aca aac tac gcg ccg gcg     192
Ala Gly Ile Lys Lys Asn Asp Gly Ser Trp Thr Asn Tyr Ala Pro Ala
        50                  55                  60 gtg cag ggc cgt gcc acc atc tcg agg gac aac ggg caa agc aca gtg     240
Val Gln Gly Arg Ala Thr Ile Ser Arg Asp Asn Gly Gln Ser Thr Val
 65                  70                  75                  80 agg ctg cag ctg aac aac ctc agg gct gac gac acc ggc atc tac gtc     288
Arg Leu Gln Leu Asn Asn Leu Arg Ala Asp Asp Thr Gly Ile Tyr Val
                85                  90                  95 tgc acc aga gat gtt aat agt ggt tac cct gat gct gct gac atc gac     336
Cys Thr Arg Asp Val Asn Ser Gly Tyr Pro Asp Ala Ala Asp Ile Asp
            100                 105                 110 gca tgg ggc cac ggg acc gaa gtc atc gtc tcc tcc                     372
Ala Trp Gly His Gly Thr Glu Val Ile Val Ser Ser
        115                 120

<210> SEQ ID NO 22
<211> LENGTH: 124
<212> TYPE: PRT
<213> ORGANISM: chicken hybridoma cell line 13C8
```

<400> SEQUENCE: 22

Ala Val Thr Leu Asp Glu Ser Gly Gly Gly Leu Gln Thr Pro Gly Gly
1               5                   10                  15

Gly Leu Ser Leu Val Cys Lys Gly Ser Gly Leu Asp Phe Ser Ser Tyr
            20                  25                  30

Ala Met Gly Trp Val Arg Gln Ala Pro Gly Lys Gly Leu Glu Phe Val
        35                  40                  45

Ala Gly Ile Lys Lys Asn Asp Gly Ser Trp Thr Asn Tyr Ala Pro Ala
    50                  55                  60

Val Gln Gly Arg Ala Thr Ile Ser Arg Asp Asn Gly Gln Ser Thr Val
65                  70                  75                  80

Arg Leu Gln Leu Asn Asn Leu Arg Ala Asp Asp Thr Gly Ile Tyr Val
                85                  90                  95

Cys Thr Arg Asp Val Asn Ser Gly Tyr Pro Asp Ala Ala Asp Ile Asp
            100                 105                 110

Ala Trp Gly His Gly Thr Glu Val Ile Val Ser Ser
        115                 120

<210> SEQ ID NO 23
<211> LENGTH: 375
<212> TYPE: DNA
<213> ORGANISM: chicken hybridoma cell line 8C3
<220> FEATURE:
<221> NAME/KEY: CDS
<222> LOCATION: (1)..(375)

<400> SEQUENCE: 23 gcc gtg acg ttg gac gag tcc ggg ggc ggc ctc cag acg ccc gga gga      48
Ala Val Thr Leu Asp Glu Ser Gly Gly Gly Leu Gln Thr Pro Gly Gly
1               5                   10                  15 ggg ctc agc ctc gtc tgc aag gcc tcc ggg ttc tct atc ggc ggt tac      96
Gly Leu Ser Leu Val Cys Lys Ala Ser Gly Phe Ser Ile Gly Gly Tyr
            20                  25                  30 atc atg cac tgg gtg cgc cag acg cct gga aag ggg ctg gaa tac gtt     144
Ile Met His Trp Val Arg Gln Thr Pro Gly Lys Gly Leu Glu Tyr Val
        35                  40                  45 gca ggt att gat gct ggt ggt ggt agc aca tac tac ggg gcg gcg gtg     192
Ala Gly Ile Asp Ala Gly Gly Gly Ser Thr Tyr Tyr Gly Ala Ala Val
    50                  55                  60 cag ggc cgt gcc acc gtc tcg agg gac aac ggg cag agc aca ctg agg     240
Gln Gly Arg Ala Thr Val Ser Arg Asp Asn Gly Gln Ser Thr Leu Arg
65                  70                  75                  80 ctg cag ctg aac aac ctc agg ctg gag gac acc ggc acc tac ttc tgc     288
Leu Gln Leu Asn Asn Leu Arg Leu Glu Asp Thr Gly Thr Tyr Phe Cys
                85                  90                  95 gcc aaa gct tct cgg tgt ggc tat gat tgg tgt tct gct gat aac atc     336
Ala Lys Ala Ser Arg Cys Gly Tyr Asp Trp Cys Ser Ala Asp Asn Ile
            100                 105                 110 gac gca tgg ggc cac ggg acc gaa gtc atc gtc tcc tcc                 375
Asp Ala Trp Gly His Gly Thr Glu Val Ile Val Ser Ser
        115                 120                 125

<210> SEQ ID NO 24
<211> LENGTH: 125
<212> TYPE: PRT
<213> ORGANISM: chicken hybridoma cell line 8C3

<400> SEQUENCE: 24

Ala Val Thr Leu Asp Glu Ser Gly Gly Gly Leu Gln Thr Pro Gly Gly
1               5                   10                  15

```
Gly Leu Ser Leu Val Cys Lys Ala Ser Gly Phe Ser Ile Gly Gly Tyr
             20                  25                  30

Ile Met His Trp Val Arg Gln Thr Pro Gly Lys Gly Leu Glu Tyr Val
         35                  40                  45

Ala Gly Ile Asp Ala Gly Gly Ser Thr Tyr Tyr Gly Ala Ala Val
     50                  55                  60

Gln Gly Arg Ala Thr Val Ser Arg Asp Asn Gln Ser Thr Leu Arg
 65                  70                  75                  80

Leu Gln Leu Asn Asn Leu Arg Leu Glu Asp Thr Gly Thr Tyr Phe Cys
                 85                  90                  95

Ala Lys Ala Ser Arg Cys Gly Tyr Asp Trp Cys Ser Ala Asp Asn Ile
            100                 105                 110

Asp Ala Trp Gly His Gly Thr Glu Val Ile Val Ser Ser
            115                 120                 125

<210> SEQ ID NO 25
<211> LENGTH: 324
<212> TYPE: DNA
<213> ORGANISM: chicken hybridoma cell line 2-1
<220> FEATURE:
<221> NAME/KEY: CDS
<222> LOCATION: (1)..(324)

<400> SEQUENCE: 25 gcg ctg act cag ccg tcc tcg gtg tca gca aac cca gga gaa acc gtc      48
Ala Leu Thr Gln Pro Ser Ser Val Ser Ala Asn Pro Gly Glu Thr Val
 1               5                  10                  15 aag atc acc tgc tcc ggg ggt ggc agc tac gct gga agt tac tat tat      96
Lys Ile Thr Cys Ser Gly Gly Gly Ser Tyr Ala Gly Ser Tyr Tyr Tyr
             20                  25                  30 ggc tgg tac cag cag aag gca cct gcc agt gcc cct gtc act gtg atc     144
Gly Trp Tyr Gln Gln Lys Ala Pro Ala Ser Ala Pro Val Thr Val Ile
         35                  40                  45 tat gac aac acc aac aga ccc tcg aac atc cct tca cga ttc tcc ggt     192
Tyr Asp Asn Thr Asn Arg Pro Ser Asn Ile Pro Ser Arg Phe Ser Gly
     50                  55                  60 tcc cta tcc ggc tcc aca aac aca tta acc atc act ggg gtc caa gtc     240
Ser Leu Ser Gly Ser Thr Asn Thr Leu Thr Ile Thr Gly Val Gln Val
 65                  70                  75                  80 gag gac gag gct gtc tat tac tgt ggg agc ttc gac agc agt tat gtt     288
Glu Asp Glu Ala Val Tyr Tyr Cys Gly Ser Phe Asp Ser Ser Tyr Val
                 85                  90                  95 ggt ata ctt ggg gcc ggg aca acc ctg acc gtc cta                     324
Gly Ile Leu Gly Ala Gly Thr Thr Leu Thr Val Leu
            100

<210> SEQ ID NO 26
<211> LENGTH: 108
<212> TYPE: PRT
<213> ORGANISM: chicken hybridoma cell line 2-1

<400> SEQUENCE: 26

Ala Leu Thr Gln Pro Ser Ser Val Ser Ala Asn Pro Gly Glu Thr Val
 1               5                  10                  15

Lys Ile Thr Cys Ser Gly Gly Gly Ser Tyr Ala Gly Ser Tyr Tyr Tyr
             20                  25                  30

Gly Trp Tyr Gln Gln Lys Ala Pro Ala Ser Ala Pro Val Thr Val Ile
         35                  40                  45

Tyr Asp Asn Thr Asn Arg Pro Ser Asn Ile Pro Ser Arg Phe Ser Gly
```

```
                    50                  55                  60
Ser Leu Ser Gly Ser Thr Asn Thr Leu Thr Ile Thr Gly Val Gln Val
 65                  70                  75                  80

Glu Asp Glu Ala Val Tyr Tyr Cys Gly Ser Phe Asp Ser Ser Tyr Val
                 85                  90                  95

Gly Ile Leu Gly Ala Gly Thr Thr Leu Thr Val Leu
            100                 105

<210> SEQ ID NO 27
<211> LENGTH: 312
<212> TYPE: DNA
<213> ORGANISM: chicken hybridoma cell line 5D11
<220> FEATURE:
<221> NAME/KEY: CDS
<222> LOCATION: (1)..(312)

<400> SEQUENCE: 27 gcg ctg act cag ccg tcc tcg gtg tca gca aac ctg gga gaa acc gtc       48
Ala Leu Thr Gln Pro Ser Ser Val Ser Ala Asn Leu Gly Glu Thr Val
 1               5                  10                  15 gaa atc acc tgc tcc ggg ggc agg tat agg tat ggc tgg tat cag cag       96
Glu Ile Thr Cys Ser Gly Gly Arg Tyr Arg Tyr Gly Trp Tyr Gln Gln
             20                  25                  30 aag tca tct ggc agt gcc cct gtc act gtg atc tat gac aac gac aag      144
Lys Ser Ser Gly Ser Ala Pro Val Thr Val Ile Tyr Asp Asn Asp Lys
         35                  40                  45 aga ccc tcg gac atc cct tca cga ttc tcc ggt tcc aaa tcc gac tcc      192
Arg Pro Ser Asp Ile Pro Ser Arg Phe Ser Gly Ser Lys Ser Asp Ser
 50                  55                  60 acg ggc aca tta acc atc act ggg gtc caa gcc gag gac gag gct gtc      240
Thr Gly Thr Leu Thr Ile Thr Gly Val Gln Ala Glu Asp Glu Ala Val
 65                  70                  75                  80 tat tac tgt ggg aat gca gac aac aat act tac gat cct ata ttt ggg      288
Tyr Tyr Cys Gly Asn Ala Asp Asn Asn Thr Tyr Asp Pro Ile Phe Gly
                 85                  90                  95 gcc ggg aca acc ctg acc gtc cta                                      312
Ala Gly Thr Thr Leu Thr Val Leu
            100

<210> SEQ ID NO 28
<211> LENGTH: 104
<212> TYPE: PRT
<213> ORGANISM: chicken hybridoma cell line 5D11

<400> SEQUENCE: 28

Ala Leu Thr Gln Pro Ser Ser Val Ser Ala Asn Leu Gly Glu Thr Val
 1               5                  10                  15

Glu Ile Thr Cys Ser Gly Gly Arg Tyr Arg Tyr Gly Trp Tyr Gln Gln
             20                  25                  30

Lys Ser Ser Gly Ser Ala Pro Val Thr Val Ile Tyr Asp Asn Asp Lys
         35                  40                  45

Arg Pro Ser Asp Ile Pro Ser Arg Phe Ser Gly Ser Lys Ser Asp Ser
 50                  55                  60

Thr Gly Thr Leu Thr Ile Thr Gly Val Gln Ala Glu Asp Glu Ala Val
 65                  70                  75                  80

Tyr Tyr Cys Gly Asn Ala Asp Asn Asn Thr Tyr Asp Pro Ile Phe Gly
                 85                  90                  95

Ala Gly Thr Thr Leu Thr Val Leu
            100
```

-continued

```
<210> SEQ ID NO 29
<211> LENGTH: 324
<212> TYPE: DNA
<213> ORGANISM: chicken hybridoma cell line 13C8
<220> FEATURE:
<221> NAME/KEY: CDS
<222> LOCATION: (1)..(324)

<400> SEQUENCE: 29 gcg ctg act cag ccg tcc tcg gtg tca gca aac ctg gga gga acc gtc      48
Ala Leu Thr Gln Pro Ser Ser Val Ser Ala Asn Leu Gly Gly Thr Val
 1               5                  10                  15 aag atc acc tgc tcc ggg ggc agc tat ggc tat ggc tgg ttc cag cag      96
Lys Ile Thr Cys Ser Gly Gly Ser Tyr Gly Tyr Gly Trp Phe Gln Gln
             20                  25                  30 aag tca cct ggc agt gcc cct gtc cct gtg atc tac tgg aac aac aag     144
Lys Ser Pro Gly Ser Ala Pro Val Pro Val Ile Tyr Trp Asn Asn Lys
         35                  40                  45 aga ccc tcg gac atc cct tca cga ttc tcc ggt tcc aaa tcc ggc tcc     192
Arg Pro Ser Asp Ile Pro Ser Arg Phe Ser Gly Ser Lys Ser Gly Ser
     50                  55                  60 aca gcc aca tta acc atc act ggg gtc cga gcc gag gac gag gct gtc     240
Thr Ala Thr Leu Thr Ile Thr Gly Val Arg Ala Glu Asp Glu Ala Val
 65                  70                  75                  80 tat tac tgt ggg aat gca gac agc aat act gct gat agt gat tat gtt     288
Tyr Tyr Cys Gly Asn Ala Asp Ser Asn Thr Ala Asp Ser Asp Tyr Val
                 85                  90                  95 ggt ata ttt ggg gcc ggg aca acc ctg acc gtc cta                     324
Gly Ile Phe Gly Ala Gly Thr Thr Leu Thr Val Leu
            100                 105

<210> SEQ ID NO 30
<211> LENGTH: 108
<212> TYPE: PRT
<213> ORGANISM: chicken hybridoma cell line 13C8

<400> SEQUENCE: 30

Ala Leu Thr Gln Pro Ser Ser Val Ser Ala Asn Leu Gly Gly Thr Val
 1               5                  10                  15

Lys Ile Thr Cys Ser Gly Gly Ser Tyr Gly Tyr Gly Trp Phe Gln Gln
             20                  25                  30

Lys Ser Pro Gly Ser Ala Pro Val Pro Val Ile Tyr Trp Asn Asn Lys
         35                  40                  45

Arg Pro Ser Asp Ile Pro Ser Arg Phe Ser Gly Ser Lys Ser Gly Ser
     50                  55                  60

Thr Ala Thr Leu Thr Ile Thr Gly Val Arg Ala Glu Asp Glu Ala Val
 65                  70                  75                  80

Tyr Tyr Cys Gly Asn Ala Asp Ser Asn Thr Ala Asp Ser Asp Tyr Val
                 85                  90                  95

Gly Ile Phe Gly Ala Gly Thr Thr Leu Thr Val Leu
            100                 105

<210> SEQ ID NO 31
<211> LENGTH: 315
<212> TYPE: DNA
<213> ORGANISM: chicken hybridoma cell line 8C3
<220> FEATURE:
<221> NAME/KEY: CDS
<222> LOCATION: (1)..(315)

<400> SEQUENCE: 31
```

```
gcg ctg act caa ccg tcc tcg gtg tca gcg atc ccg gga gaa acc gtc      48
Ala Leu Thr Gln Pro Ser Ser Val Ser Ala Ile Pro Gly Glu Thr Val
 1               5                  10                  15 gag atc acc tgc tcc ggg ggt aac aac tac tat ggc tgg tat cag cag      96
Glu Ile Thr Cys Ser Gly Gly Asn Asn Tyr Tyr Gly Trp Tyr Gln Gln
             20                  25                  30 aaa tca cct ggc agt gcc cct gtc act gtg atc tac tac aac aac aag     144
Lys Ser Pro Gly Ser Ala Pro Val Thr Val Ile Tyr Tyr Asn Asn Lys
         35                  40                  45 aga ccc tcg gac atc cct tca cga ttc tcc ggt tcc aaa ccc ggc tcc     192
Arg Pro Ser Asp Ile Pro Ser Arg Phe Ser Gly Ser Lys Pro Gly Ser
     50                  55                  60 aca aac aca tta acc atc act ggg gtc cga gcc gag gac gag gct gtc     240
Thr Asn Thr Leu Thr Ile Thr Gly Val Arg Ala Glu Asp Glu Ala Val
 65                  70                  75                  80 tat ttc tgt ggt gcc tgg gaa agt agt cct att tat gtt ggt ata ttt     288
Tyr Phe Cys Gly Ala Trp Glu Ser Ser Pro Ile Tyr Val Gly Ile Phe
                 85                  90                  95 ggg gcc ggg aca acc ctg acc gtc cta                                  315
Gly Ala Gly Thr Thr Leu Thr Val Leu
                100                 105
```

<210> SEQ ID NO 32
<211> LENGTH: 105
<212> TYPE: PRT
<213> ORGANISM: chicken hybridoma cell line 8C3

<400> SEQUENCE: 32

```
Ala Leu Thr Gln Pro Ser Ser Val Ser Ala Ile Pro Gly Glu Thr Val
 1               5                  10                  15

Glu Ile Thr Cys Ser Gly Gly Asn Asn Tyr Tyr Gly Trp Tyr Gln Gln
             20                  25                  30

Lys Ser Pro Gly Ser Ala Pro Val Thr Val Ile Tyr Tyr Asn Asn Lys
         35                  40                  45

Arg Pro Ser Asp Ile Pro Ser Arg Phe Ser Gly Ser Lys Pro Gly Ser
     50                  55                  60

Thr Asn Thr Leu Thr Ile Thr Gly Val Arg Ala Glu Asp Glu Ala Val
 65                  70                  75                  80

Tyr Phe Cys Gly Ala Trp Glu Ser Ser Pro Ile Tyr Val Gly Ile Phe
                 85                  90                  95

Gly Ala Gly Thr Thr Leu Thr Val Leu
                100                 105
```

<210> SEQ ID NO 33
<211> LENGTH: 7
<212> TYPE: PRT
<213> ORGANISM: Artificial Sequence
<220> FEATURE:
<223> OTHER INFORMATION: reverse primer for PCR amplification of heavy
      chain variable region

<400> SEQUENCE: 33

```
Ala Val Thr Leu Asp Glu Ser
 1               5
```

<210> SEQ ID NO 34
<211> LENGTH: 7
<212> TYPE: PRT
<213> ORGANISM: Artificial Sequence
<220> FEATURE:
<223> OTHER INFORMATION: forward primer for PCR amplification of heavy
      chain variable region -continued

```
<400> SEQUENCE: 34

Ser Ser Val Ile Val Glu Thr
 1               5

<210> SEQ ID NO 35
<211> LENGTH: 7
<212> TYPE: PRT
<213> ORGANISM: Artificial Sequence
<220> FEATURE:
<223> OTHER INFORMATION: reverse primer for PCR amplification of light
      chain variable region

<400> SEQUENCE: 35

Ala Leu Thr Gln Pro Ser Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: forward primer for PCR amplification of light
      chain variable region

<400> SEQUENCE: 36

Leu Val Thr Leu Thr Thr Gly
 1               5

<210> SEQ ID NO 37
<211> LENGTH: 381
<212> TYPE: DNA
<213> ORGANISM: chicken hybridoma cell line 6D-12-G10
<220> FEATURE:
<221> NAME/KEY: CDS
<222> LOCATION: (1)..(381)

<400> SEQUENCE: 37 gcc gtg acg ttg gac gag tcc ggg ggc ggc ctc cag acg ccc gga aga      48
Ala Val Thr Leu Asp Glu Ser Gly Gly Gly Leu Gln Thr Pro Gly Arg
 1               5                  10                  15 gcg ctc agc ctc gtc tgc aag gcc tcc ggg ttc acc ttc agc agt tat      96
Ala Leu Ser Leu Val Cys Lys Ala Ser Gly Phe Thr Phe Ser Ser Tyr
             20                  25                  30 ggc atg gtc tgg gtg cga cag gcg ccc ggc aag ggg ctg gaa tac gtc     144
Gly Met Val Trp Val Arg Gln Ala Pro Gly Lys Gly Leu Glu Tyr Val
         35                  40                  45 gct gaa att atc aca act ggt aga gac aca tgg tat ggg acg gcg gtg     192
Ala Glu Ile Ile Thr Thr Gly Arg Asp Thr Trp Tyr Gly Thr Ala Val
     50                  55                  60 aag ggc cgt gcc acc atc tcg agg gac aac ggg cag agt aca gtg agg     240
Lys Gly Arg Ala Thr Ile Ser Arg Asp Asn Gly Gln Ser Thr Val Arg
 65                  70                  75                  80 ctg cag ctg aac aac ctc agg gct gaa gac acc ggc atc tac tac tgc     288
Leu Gln Leu Asn Asn Leu Arg Ala Glu Asp Thr Gly Ile Tyr Tyr Cys
                 85                  90                  95 gcc aaa tgc agt tat gag tgt act agt agt tgt tgg ggt tat act gat     336
Ala Lys Cys Ser Tyr Glu Cys Thr Ser Ser Cys Trp Gly Tyr Thr Asp
            100                 105                 110 atg atc gac gca tgg ggc cac ggg acc gaa gtc atc gtc tcc tcc         381
Met Ile Asp Ala Trp Gly His Gly Thr Glu Val Ile Val Ser Ser
        115                 120                 125

<210> SEQ ID NO 38
```

<211> LENGTH: 127
<212> TYPE: PRT
<213> ORGANISM: chicken hybridoma cell line 6D-12-G10

<400> SEQUENCE: 38

```
Ala Val Thr Leu Asp Glu Ser Gly Gly Leu Gln Thr Pro Gly Arg
 1               5                  10                  15

Ala Leu Ser Leu Val Cys Lys Ala Ser Gly Phe Thr Phe Ser Ser Tyr
            20                  25                  30

Gly Met Val Trp Val Arg Gln Ala Pro Gly Lys Gly Leu Glu Tyr Val
        35                  40                  45

Ala Glu Ile Ile Thr Thr Gly Arg Asp Thr Trp Tyr Gly Thr Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Ile Tyr Tyr Cys
                85                  90                  95

Ala Lys Cys Ser Tyr Glu Cys Thr Ser Ser Cys Trp Gly Tyr Thr Asp
            100                 105                 110

Met Ile Asp Ala Trp Gly His Gly Thr Glu Val Ile Val Ser Ser
        115                 120                 125
```

<210> SEQ ID NO 39
<211> LENGTH: 312
<212> TYPE: DNA
<213> ORGANISM: chicken hybridoma cell line 6D-12-G10
<220> FEATURE:
<221> NAME/KEY: CDS
<222> LOCATION: (1)..(312)

<400> SEQUENCE: 39

```
gcg ctg act cag ccg tcc tcg gtg tca gca aac ctg gga gga acc gtc      48
Ala Leu Thr Gln Pro Ser Ser Val Ser Ala Asn Leu Gly Gly Thr Val
 1               5                  10                  15 aag atc acc tgc tcc ggg agt agt ggc agc tat ggc tgg tat cag cag      96
Lys Ile Thr Cys Ser Gly Ser Ser Gly Ser Tyr Gly Trp Tyr Gln Gln
            20                  25                  30 aag tca cct ggc agt gcc cct gtc act gtg atc tat tac aac gac aag     144
Lys Ser Pro Gly Ser Ala Pro Val Thr Val Ile Tyr Tyr Asn Asp Lys
        35                  40                  45 aga ccc tcg gac atc cct tca cga ttc tcc ggt tcc aaa tcc ggc tcc     192
Arg Pro Ser Asp Ile Pro Ser Arg Phe Ser Gly Ser Lys Ser Gly Ser
    50                  55                  60 acg ggc aca tta acc atc act ggg gtc caa gcc gag gac gag gct gtc     240
Thr Gly Thr Leu Thr Ile Thr Gly Val Gln Ala Glu Asp Glu Ala Val
65                  70                  75                  80 tat ttc tgt gag agt aca gac tac agt agt act gat ata ttt ggg gcc     288
Tyr Phe Cys Glu Ser Thr Asp Tyr Ser Ser Thr Asp Ile Phe Gly Ala
                85                  90                  95 ggg aca acc ctg acc gtc cta ggt                                     312
Gly Thr Thr Leu Thr Val Leu Gly
            100
```

<210> SEQ ID NO 40
<211> LENGTH: 104
<212> TYPE: PRT
<213> ORGANISM: chicken hybridoma cell line 6D-12-G10

<400> SEQUENCE: 40

```
Ala Leu Thr Gln Pro Ser Ser Val Ser Ala Asn Leu Gly Gly Thr Val
 1               5                  10                  15
```

-continued

```
Lys Ile Thr Cys Ser Gly Ser Ser Gly Ser Tyr Gly Trp Tyr Gln Gln
             20                  25                  30

Lys Ser Pro Gly Ser Ala Pro Val Thr Val Ile Tyr Tyr Asn Asp Lys
             35                  40                  45

Arg Pro Ser Asp Ile Pro Ser Arg Phe Ser Gly Ser Lys Ser Gly Ser
         50                  55                  60

Thr Gly Thr Leu Thr Ile Thr Gly Val Gln Ala Glu Asp Glu Ala Val
 65                  70                  75                  80

Tyr Phe Cys Glu Ser Thr Asp Tyr Ser Ser Thr Asp Ile Phe Gly Ala
                 85                  90                  95

Gly Thr Thr Leu Thr Val Leu Gly
            100
```

What is claimed is:

1. A recombinant scFv antibody capable of binding to a sporozoite 12kd surface antigen from Eimeria acervulina, which comprises a heavy chain variable region comprising the amino acid sequence of SEQ ID NO:18 and a light chain variable region comprising the amino acid sequence of SEQ ID NO:26, wherein the recombinant scFv antibody comprises a linker between the heavy chain variable region and the light chain variable region.

2. An scFv antibody capable of binding to a sporozoite 12kd surface antigen from Emimeria acervulina, which comprises a heavy chain variable region comprising the amino acid sequence of SEQ ID NO:18 and a light chain variable region comprising the amino acid sequence of SEQ ID NO:26.

* * * * *